(12) United States Patent
Shuke

(10) Patent No.: US 8,483,468 B2
(45) Date of Patent: Jul. 9, 2013

(54) APPARATUS, PROGRAM AND METHOD FOR DETERMINING CEREBRAL BLOOD FLOW

(75) Inventor: Noriyuki Shuke, Hokkaido (JP)

(73) Assignees: Nihon Medi-Physics Co., Ltd., Tokyo (JP); Noriyuki Shuke, Hokkaido (JP)

( * ) Notice: Subject to any disclaimer, the term of this patent is extended or adjusted under 35 U.S.C. 154(b) by 0 days.

(21) Appl. No.: 13/270,420

(22) Filed: Oct. 11, 2011

(65) Prior Publication Data

US 2012/0183192 A1  Jul. 19, 2012

(30) Foreign Application Priority Data

Oct. 19, 2010 (JP) ................................. 2010-247875

(51) Int. Cl.
*G06K 9/00* (2006.01)
*G01N 23/00* (2006.01)

(52) U.S. Cl.
USPC .................................. 382/131; 378/4; 378/8

(58) Field of Classification Search
None
See application file for complete search history.

(56) References Cited

U.S. PATENT DOCUMENTS

| | | | |
|---|---|---|---|
| 2005/0113680 A1* | 5/2005 | Ikeda et al. | 600/425 |
| 2008/0128626 A1* | 6/2008 | Rousso et al. | 250/362 |
| 2011/0150309 A1* | 6/2011 | Barfett et al. | 382/131 |

FOREIGN PATENT DOCUMENTS

JP  2004239782  * 8/2004

OTHER PUBLICATIONS

Hashikawa et al., "Split dose iodine-123-IMP SPECT: sequential quantitative regional cerebral blood flow change with pharmacological intervention," Journal of Nuclear Medicine, Jul. 1994, 35(7), 1226-1233.

Iida et al., "Quantitative mapping of regional cerebral blood flow using iodine-123-IMP and SPECT," The Journal of Nuclear Medicine, Dec. 1994, 35(12), 2019-2030.

(Continued)

*Primary Examiner* — Nancy Bitar
(74) *Attorney, Agent, or Firm* — Woodcock Washburn LLP

(57) ABSTRACT

[Object] To provide a method for accurately determining cerebral blood flows both in rest state and under medication with less invasive operations.

[Solution] Cerebral blood flow is determined based on a formula represented by the following formulas (1) or (2) for a time under medication that continuously follows a resting time.

$$B(t) = k_1 e^{-k_2 t_3} mC_f \int_0^{t_3} S(\tau) e^{k_2 \tau} d\tau (e^{-k_{2d}(t-t_3)}) + \quad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B(t) dt = \quad (2)$$

$$\frac{k_1}{k_{2d}} e^{-k_2 t_3} mC_f \int_0^{t_3} S(\tau) e^{k_2 \tau} d\tau \cdot (e^{-k_{2d}(t_5-t_3)} - e^{-k_{2d}(t_6-t_3)}) +$$

$$\int_{t_5}^{t_6} k_{1d} mC_f \int_{t_3}^{t} (S(\tau) + S(\tau - t_3)) \cdot e^{-k_{2d} \cdot (t-\tau)} d\tau dt (t \geq t_3)$$

(B(t): the radiation count at the time of t, $t_3$: the time when a radioisotope medicine is administered, $t_5$: the time when acquisition of the imaging data started for the state under medication, $t_6$: the time when acquisition of the imaging data finished for the state under medication, $mC_f$: a scaling factor, $k_1$: cerebral blood flow rest state, $k_2$: the blood-outflow-rate-constant of brain tissues rest state, $k_{1d}$: a cerebral blood flow under medication, and $k_{2d}$: the blood-outflow-rate-constant of brain tissues under medication).

12 Claims, 8 Drawing Sheets

OTHER PUBLICATIONS

Kawamura, Y., "Estimation by static SPECT of the radioactivity remaining after the first dose of two-fractionated 123I-IMP administration: the rate of increase in cerebral blood flow by ARG and the rate of increase in SPECT count," Japanese Journal of Nuclear Medicine, May 2002, 39(2), 125-134 (English Abstract Included).

Kim et al., "Quantitative mapping of basal and vasareactive cerebral blood flow using split-dose 123I-iodoamphetamine and single photon emission computed tomography," Neuroimage, Dec. 2006, 33(4), 1126-1135.

* cited by examiner

APPARATUS, PROGRAM AND METHOD FOR DETERMINING CEREBRAL BLOOD FLOW

TECHNOLOGICAL FIELD

The present invention relates to an apparatus, a program, and methods for determining cerebral blood flow based on nuclear medicine brain imaging.

BACKGROUND

Cerebrovascular disorders such as cerebral infarction occupy the top ranks in terms of cause of death. If the discovery timing of treatment is delayed, sometimes serious sequelae remain. Therefore, early discovery of cerebrovascular disorders and diagnosis of the degree of seriousness are extremely important.

The nuclear medicine image diagnostic techniques such as SPECT, MRI, CT, and etc. are known as a main diagnostic technique for cerebrovascular disorders. The nuclear medicine image diagnostic techniques make finding the amount of cerebral blood flow at the tissue level relatively easily. That is why these techniques are widely used in the early diagnosis of cerebrovascular disorders and diagnosis for the degree of seriousness.

The Microsphere method and IMP-ARG method are mainly used as diagnosing cerebrovascular disorders using the nuclear medicine image diagnostic technique. In the Microsphere method, a cerebral blood flow-preparation product at an early stage following administration is regarded as a Microsphere and the local cerebral blood flow is obtained from nuclear medicine image data based on a one-compartment model. The advantages of this method are its straightforward theory and easy calculation; however, there are disadvantages such as its highly invasive properties due to the necessity of continuous blood sampling of arterial blood. Furthermore, because the move of drugs from tissues into the blood vessels is not taken into consideration, the determining accuracy in the later stages after the drug is administered deteriorates, creating a further disadvantage in that the point of data collection time is limited to the relatively early stages after having been administered.

Instead of the continuous blood sampling of arterial blood, the NIMS method has been proposed in which an input function is estimated using a time activity curve based on dynamic planar data of the chest part; however, this method is also based on the one-compartment model, preventing sufficient determining accuracy from being obtained at the later stages after the drug is administered.

On the other hand, the IMP-ARG method is a method for obtaining cerebral blood flow according to the Look-up table approach by administering IMP (N-Isopropyl-4-[$^{123}$I]Iodoamphetamine hydrochloride) as a radioisotope medicine and substituting a count after a certain time has elapsed in a formula of a two-compartment model in the nuclear medicine brain imaging (Non-patent Document 1). With the IMP-ARG method, a method for correcting the standard input function may be used by obtaining blood sample data of an artery at one point, providing an advantage of being less invasive than the Microsphere method for which continuous blood sampling data is required.

[Non-patent Document 1]

Hidehiro Iida et al, "Quantative Mapping of Regional; Cerebral Blood Flow Using Iodine-123-IMP and SPECT", The Journal of Nuclear Medicine, December 1994, Vol. 35, No. 12, pp 2019-2030

[Non-patent Document 2]

Kyeong Min Kim et al., "Quantitative Mapping of basal and vasareactive cerebral blood flow using split-dose 123I-iodoamphetamine and single photon emission computed tomography.", NeuroImage, 2006, Vol. 33, pp 1126-1135

[Non-patent Document 3]

Kazuo Hashikawa et al., "Split Dose Iodine-123-IMP SPECT: Sequential Quantitative Regional Cerebral Blood Flow Change with Pharmacological Intervention.", Journal of Nuclear Medicine, July 1994, Vol. 35, No. 7, pp 1226-1233

[Non-patent Document 4]

Yoshifumi Kawamura "A method for estimating radiation remaining in the brain using static-SPECT after the first time when 123I-IMP is administered in a two occasion-study on the ARG method cerebral blood flow increase rate and the SPECT count increase rate-" Nuclear Medicine, 2002, Vol. 39. pp 125-134

With the IMP-ARG method, sometimes changes in sought values due to the injection of a drug with vasodilator action such as acetazolamide, etc. are measured for the purpose of evaluating the circulation reserve ability of cerebral blood vessels. In this case, SPECT measurements have to be performed in two occasions, for the case in which acetazolamide has been administered (under medication) and the case in which it has not been administered (rest state). Here, it is necessary to wait for sufficient clearance time after the finish of cerebral blood flow SPECT imaging in rest state to perform cerebral blood flow SPECT imaging under medication. However, it needs two days to perform the cerebral blood flow SPECT imaging under medication after waiting for sufficient clearance from the finish of the cerebral blood flow SPECT imaging in rest state. So it puts significant burden onto a subject as well as onto the medical institutions performing the test. With such a background, various methods of performing a SPECT test in one day both in rest state and under medication have been studied and clinically applied (Non-patent Documents 2 to 4).

As described above, the IMP-ARG method is one of the best diagnostic techniques for cerebrovascular disorders. However, even with the IMP-ARG method, blood sampling of arterial blood is required. In general, blood sampling of arterial blood is more invasive than blood sampling of venous blood. With such a background, it has been desired to realize a technique for determining the amount of cerebral blood flow by less invasive operations. But no such method had been known. Furthermore, if venous blood is mixed in when blood sampling of arterial blood is taking place, there is a problem in that the reliability of the obtained data deteriorates.

Moreover, for evaluating the circulation reserve ability of cerebral blood vessels, it is necessary to obtain count changes under medication without being influenced by the radioisotope medicine that is administered during SPECT measurement in rest state. In this case, in terms of reducing the burden on the subject and the examining institution, it is desired to perform the test within one day. Consequently, various techniques such as the one described in the above non-patent documents have been developed. In order to fully satisfy such a need with respect to performing the test within a day, proposing a new method that has not been developed has significant values in and of itself. Furthermore, there was no technique for determining cerebral blood flow which performs both the test in the rest state and the test under medication within a day, while it does not need to sample the arterial blood.

The present invention has been designed in view of the above situation and with the purpose of providing a technique for accurately determining cerebral blood flow by less invasive means capable of performing a plurality of SPECT tests in a single day.

SUMMARY OF THE INVENTION

The inventors completed the present invention as a result of studying a two-compartment model used for determining cerebral blood flow in detail and proposing theoretical formulas applicable to the case in which a plurality of SPECT tests are consecutively performed.

Following jargons are herein defined.

Input function: a function representing temporal changes in the concentration of a radioisotope medicine in arterial blood, which determines the amount of radiation inflow into a subject organ.

Standard input function: a function representing temporal changes in the amount of standard inflow of a radioisotope medicine into the brain, that is, a standardized input function using an input function that is determined based on actual measured values among a plurality of subjects. For example, this is created by averaging the input functions of the plurality of subjects.

Scaling factor: a correction coefficient to correct measurement sensitivity for analyzing head part image data by approximating a standard input function to an input function in a subject.

Cerebral-blood-distribution-coefficient ($V_d$): the ratio ($k_1/k_2$) of the cerebral blood flow ($k_1$) and the blood-outflow-rate-constant of brain tissues (flux of the radiation count washed out into the blood from brain tissues) ($k_2$) in a two-compartment model ($k_1/k_2$).

Not only SPECT images but also PET images or planar images can be the nuclear-medicine-brain-images intended by the present invention. These images are appropriately selected according to the type of radioisotope medicine to be used or the purpose of diagnosis.

It should be noted that the same symbols used in the following description are used to represent the same meaning unless otherwise specified. Furthermore, each time unit used in each formula represents the elapsed time when the time for the first radioisotope-drug-injection is 0.

An apparatus for determining cerebral blood flow as an exemplary embodiment is an apparatus for determining cerebral blood flow for determining cerebral blood flow based on first nuclear-medicine-brain-imaging-data resulting from a first radioisotope-drug-injection and second nuclear-medicine-brain-imaging-data resulting from a second radioisotope-drug-injection, and may comprise a database for storing at least a standard input function S(t), a nuclear medicine image data-obtaining part for obtaining the first and second nuclear-medicine-brain-imaging-data from a subject, and a second cerebral blood flow-calculation part for obtaining the cerebral blood flow $k_{1d}$ by applying the following formulas (1) or (2):

$$B_d(t) = k_1 e^{-k_2 t_3} mC_f \int_0^{t_3} S(\tau) e^{k_2 \tau} d\tau (e^{-k_{2d}(t-t_3)}) + k_{1d} mC_f \int_{t_3}^{t} (S(\tau) + S(\tau - t_3)) \cdot e^{-k_{2d} \cdot (t-\tau)} d\tau (t \geq t_3) \quad (1)$$

$$\int_{t_5}^{t_6} B_d(t)dt = \frac{k_1}{k_{2d}} e^{-k_2 t_3} mC_f \int_{t_0}^{t_3} S(\tau) e^{k_2 \tau} d\tau \cdot (e^{-k_{2d}(t_5 - t_3)} - e^{-k_{2d}(t_6 - t_3)}) + \int_{t_5}^{t_6} k_{1d} mC_f \int_{t_3}^{t} (S(\tau) + S(\tau - t_3)) \cdot e^{-k_{2d} \cdot (t-\tau)} d\tau dt (t \geq t_3) \quad (2)$$

to the obtained second nuclear-medicine-brain-imaging-data, and a display part for displaying the calculated cerebral blood flow $k_{1d}$.

(Here, B(t): the radiation count at the time of t, obtained from a certain cerebral region of the second brain nuclear medicine data, $t_3$: time of the injection of a radioisotope medicine when the second brain nuclear medicine data is being acquired, $t_5$: time when the second nuclear medicine brain imaging started, $t_6$: time when the second nuclear medicine brain imaging finished, $mC_f$: the scaling factor, $k_1$: the cerebral blood flow when the first nuclear-medicine-brain-imaging-data is being acquired, $k_2$: the blood-outflow-rate-constant of brain tissues when the first nuclear-medicine-brain-imaging-data is being acquired, $k_{1d}$: the cerebral blood flow when the second nuclear-medicine-brain-imaging-data is being acquired, and $k_{2d}$: the blood-outflow-rate-constant of brain tissues when the second nuclear-medicine-brain-imaging-data is being acquired)

Because of utilizing the above formulas (1) or (2) in determining cerebral blood flow using the second nuclear-medicine-brain-imaging-data, the cerebral blood flow k1d can be sought without being influenced by a radioisotope drug that has been administered when the first nuclear-medicine-brain-imaging-data is acquired. Consequently, it becomes possible to perform the second brain nuclear medicine test based on the second radioisotope-drug-injection without waiting for the radioisotope drug, administered when the first nuclear-medicine-brain-imaging-data was acquired, to be cleared from the subject's body, allowing the burden on the subject and the medical institution to be significantly reduced.

In the above formulas (1) and (2), it is possible to employ values preliminarily obtained based on the first nuclear-medicine-brain-imaging-data may be used for the cerebral blood flow $k_1$ and the blood-outflow-rate-constant from brain tissues $k_2$ at the time when the first nuclear-medicine-brain-imaging-data was acquired. The calculations of the formulas (1) or (2) can be performed by creating a table which is described later. The calculations of the formulas (1) or (2) can also be performed by means of fitting, if the radiation count is high enough.

The apparatus for determining cerebral blood flow as an exemplary embodiment may further comprise a first cerebral blood flow-calculation part for obtaining the cerebral blood flow $k_1$ by applying the following formulas (3) or (4):

$$B(t) = k_1 mC_f \int_{t_0}^{t} S(\tau) \cdot e^{-\frac{k_1}{V_d}(t-\tau)} dt \quad (3)$$

$$\int_{t_1}^{t_2} B(t)dt = \int_{t_1}^{t_2} k_1 mC_f \int_{t_0}^{t} S(\tau) \cdot e^{-\frac{k_1}{V_d}(t-\tau)} d\tau dt \quad (4)$$

to the first nuclear-medicine-brain-imaging-data obtained in the nuclear medicine image data-obtaining part. (Here, B(t): the radiation count obtained from a certain cerebral region of the first brain nuclear medicine data at the time of t, $t_1$: the time when the first nuclear medicine brain imaging started, $t_2$: the time when the first nuclear medicine brain imaging finished, and $V_d$: the cerebral-blood-distribution-coefficient.) In this case, the display part displays $k_1$ in addition to $k_{1d}$. Because the first nuclear-medicine-brain-imaging-data is acquired prior to the second radioisotope-drug-injection, naturally $t \leq t_3$ in the formulas (3) and (4).

The calculated $k_1$ and $k_{1d}$ may be used for evaluation of circulatory reserve ability.

The apparatus for determining cerebral blood flow as an exemplary embodiment is configured to store, in the database, data for each of at least the following (i) and (ii):
  (i) Standard input function S(t): the function representing temporal changes in the standard inflow of a radioisotope medicine into the brain.
  (ii) Correlation formula: the correlation formula expressing the relation between $mC_f$ and $C_f \cdot V_d$.
($mC_f$: the scaling factor, $C_f$: the scaling factor obtained based on the time activity curve of the nuclear medicine brain imaging, and $V_d$: the cerebral-blood-distribution-coefficient), and may further comprise a part for creating a time activity curve representing temporal changes in counts based on the first nuclear-medicine-brain-imaging-data that is obtained in the nuclear medicine image data-obtaining part, a first parameter-calculation part for seeking $k_1 C_f$ and $k_2$ by fitting the following formula (5):

$$B(t) = k_1 C_f \int_{t_0}^{t} S(\tau) \cdot e^{-k_2 \cdot (t-\tau)} d\tau \qquad (5)$$

into the time activity curve, a second parameter-calculation part for seeking $C_f \cdot V_d$ based on the following formula (6):

$$k_1 C_f / k_2 = C_f V_d \qquad (6)$$

from the sought $k_1 C_f$ and $k_2$, and a third parameter-calculation part for seeking $mC_f$ from the $C_r \cdot V_d$ obtained in the second parameter-calculation part and the correlation formula stored in the database. Here, B(t) in formula (5) is the radiation count at the time of t, obtained from a certain cerebral region of the first brain nuclear medicine data. The cerebral region in obtaining B(t) in formula (5) and the cerebral region in obtaining B(t) in formulas (1) to (4) may be different. For example, the cerebral region for obtaining B(t) in formula (5) may be the entire brain. Therefore, the cerebral blood flow $k_1$ in formulas (1) to (4) may be different from the cerebral blood flow $k_1$ in formula (5).

Because of such a construction, it is possible to obtain the scaling factor ($mC_f$) to be used for correcting a standard input function based on a time activity curve of nuclear medicine brain imaging for determining cerebral blood flow using nuclear medicine brain imaging, allowing invasive arterial blood sampling to be omitted. Consequently, not only is it possible to reduce the burden put on a subject, but variations in resulting values based on human errors at the time of sampling arterial blood may also be prevented.

In the exemplary embodiment, the time activity curve subjected to fitting with the above formula (5) may be created based on a transversal image (slice) from the parietal lobe to the cerebellum tent. For example, it may be created by extracting a voxel which is a value between a certain upper limit count value and a certain lower limit count value from the transversal image, and using the average value of radiation counts in the extracted voxel or the total sum. Preferably the time activity curve may be created based on a transversal (slice) of a site that covers the entire ventricle from the parietal lobe to the cerebellum. According to such construction, it is possible to collect radiation counts of the cerebral blood flow robustly to create the time activity curve, making it possible to seek $mC_f$ with better accuracy.

Furthermore, in the exemplary embodiment, the correlation formula to be stored in the database may also be represented by the following formula (7).

$$mC_f = R \cdot C_f \cdot V_d + \alpha \qquad (7)$$

(in the formula, R is a proportional constant and $\alpha$ is a constant)

According to the research by the inventors, there is a substantial proportional relationship exists between the scaling factor ($mC_f$) and $C_f \cdot V_d$. Therefore, as a result of using a formula in the above formula (7) as a correlation formula, it becomes possible to represent the relation between the scaling factor ($mC_f$) and $C_f \cdot V_d$ as a simple linear relationship, making it possible to obtain the scaling factor ($mC_f$) more easily.

Furthermore, in the apparatus for determining cerebral blood flow of the exemplary embodiment, the first cerebral blood flow-calculation part and the second cerebral blood flow-calculation part calculate the cerebral blood flow $k_1$ and $k_{1d}$ per unit region of the brain, and it is also possible to configure the apparatus such that the display part displays the cerebral blood flow $k_1$ and $k_{1d}$ calculated by the first cerebral blood flow-calculation part and the second cerebral blood flow-calculation part by linking them to a corresponding unit region.

According to such construction, it becomes possible to seek and display the local cerebral blood flow of a subject, making it possible to evaluate circulatory reserve ability into greater detail.

The cerebral blood flow-determining program as an exemplary embodiment is a computer program to operate a computer comprising a storing means and a CPU, capable of using first nuclear-medicine-brain-imaging-data resulting from a first radioisotope-drug-injection as well as second nuclear-medicine-brain-imaging-data based on a subsequent second radioisotope-drug-injection and a standard input function stored in the database. The computer program causes the computer, by being executed by the CPU, to be functioned as a nuclear medicine image data-obtaining part for obtaining the first nuclear-medicine-brain-imaging-data and the second nuclear-medicine-brain-imaging-data of a subject, a second cerebral blood flow-calculation part for obtaining the cerebral blood flow $k_{1d}$ by applying the following formulas (1) or (2):

$$B_d(t) = k_1 e^{-k_2 t_3} mC_f \int_{t_0}^{t_3} S(\tau) e^{k_2 \tau} d\tau (e^{-k_{2d}(t-t_3)}) + \qquad (1)$$
$$k_{1d} mC_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B_d(t) dt = \qquad (2)$$
$$\frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) +$$
$$\int_{t_5}^{t_6} k_{1d} mC_f \int_{t_3}^{t} (S(\tau) + S(\tau - t_3)) \cdot e^{-k_{2d}(t-\tau)} d\tau dt (t \geq t_3)$$

to the obtained second nuclear-medicine-brain-imaging-data, and a display part for displaying the calculated cerebral blood flow $k_{1d}$. Here, it is possible to employ values obtained from the first nuclear-medicine-brain-imaging-data in advance for the cerebral blood flow $k_1$ and the blood-outflow-rate-constant from brain tissues $k_2$ corresponding to the time period the first nuclear-medicine-brain-image data being acquired. The calculation of $k_{1d}$ may be performed by creating a table as explained later. The calculation of $k_{1d}$ may also be performed by fitting, if the radiation count is high enough.

The cerebral blood flow-determining program as an exemplary embodiment may also be configured to operate the computer as a first cerebral blood flow-calculation part for obtaining the cerebral blood flow $k_1$ by applying the following formulas (3) or (4):

$$B(t) = k_1 m C_f \int_{t_0}^{t} S(\tau) \cdot e^{-\frac{k_1}{V_d}(t-\tau)} d\tau \quad (3)$$

$$\int_{t_1}^{t_2} B(t) dt = \int_{t_1}^{t_2} k_1 m C_f \int_{t_0}^{t} S(\tau) \cdot e^{-\frac{k_1}{V_d}(t-\tau)} d\tau dt \quad (4)$$

to the first nuclear-medicine-brain-imaging-data. Here, the above-mentioned display part is configured to display $k_1$ in addition to the cerebral blood flow $k_{1d}$, as in the embodiment of the apparatus for determining cerebral blood flow described above.

The cerebral blood flow-determining program as an exemplary embodiment is a computer program to operate a computer comprising a storage means and a CPU capable of using first nuclear-medicine-brain-imaging-data resulting from a first radioisotope-drug-injection as well as second nuclear-medicine-brain-imaging-data based on a subsequent second radioisotope-drug-injection, a correlation formula expressing the relationship between $mC_f$ and $C_f V_d$ stored in the database, and a standard input function. Said computer program may be configured to cause the computer, by being executed by the CPU, to be functioned as a nuclear medicine image data-obtaining part for obtaining the first nuclear-medicine-brain-imaging-data and the second nuclear-medicine-brain-imaging-data of a subject, a part for creating a time activity curve representing temporal changes in counts based on the obtained first nuclear-medicine-brain-imaging-data, a first parameter-calculation part for seeking $k_1 C_f$ and $k_2$ by fitting the following formula (5):

$$B(t) = k_1 C_f \int_{t_0}^{t} S(\tau) \cdot e^{-k_2 \cdot (t-\tau)} d\tau \quad (5)$$

into the time activity curve, a second parameter-calculation part for seeking $C_f V_d$ based on the following formula (6):

$$k_1 C_f / k_2 = C_f V_d \quad (6)$$

from the sought $C_f V_d$, and $k_2$ and $C_f V_d$ and, a third parameter-calculation part for seeking $mC_f$ from $C_f V_d$ obtained by the second parameter-calculation part and the correlation formula stored in the database.

In addition, it is of course possible for the cerebral blood flow-determining program as an exemplary embodiment to comprise various configurations that can be provided with the apparatus for determining cerebral blood flow of the exemplary embodiment.

In short, the computer program just has to be capable of operating a computer as an apparatus for determining cerebral blood flow of the exemplary embodiment.

A cerebral blood flow-determining method as an exemplary embodiment is a method for determining cerebral blood flow by a computer based on first nuclear-medicine-brain-imaging-data resulting from a first radioisotope-drug-injection and second nuclear-medicine-brain-imaging-data based on a subsequent second radioisotope-drug-injection, and the computer sequentially executes a nuclear medicine image data-obtaining process for obtaining the first nuclear-medicine-brain-imaging-data and the second nuclear-medicine-brain-imaging-data of a subject, a second cerebral blood flow-calculation process for obtaining the cerebral blood flow $k_{1d}$ by applying the following formulas (1) or (2):

$$B_d(t) = k_1 e^{-k_2 t_3} m C_f \int_{t_0}^{t_3} S(\tau) e^{k_2 \tau} d\tau (e^{-k_{2d}(t-t_3)}) + \quad (1)$$
$$k_{1d} m C_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B_d(t) dt = \quad (2)$$
$$\frac{k_1}{k_{2d}} e^{-k_2 t_3} m C_f \int_{t_0}^{t_3} S(\tau) e^{k_2 \tau} d\tau \cdot (e^{-k_{2d}(t_5-t_3)} - e^{-k_{2d}(t_6-t_3)}) +$$
$$\int_{t_5}^{t_6} k_{1d} m C_f \int_{t_3}^{t} (S(\tau) + S(\tau - t_3)) \cdot e^{-k_{2d}(t-\tau)} d\tau dt (t \geq t_3)$$

to the obtained second nuclear-medicine-brain-imaging-data, and a display process for displaying the calculated $k_{1d}$. Here, the values obtained based on the first nuclear-medicine-brain-imaging-data in advance may be used as the cerebral blood flow $k_1$ and the blood-outflow-rate-constant from brain tissues $k_2$ corresponding to the first nuclear-medicine-brain-image data. The calculation of $k_{1d}$ may be performed by creating a table as explained later. The calculation of $k_{1d}$ may also be performed by fitting, if the radiation count is high enough.

In the cerebral blood flow-determining method as an exemplary embodiment, prior to the above second cerebral blood flow-calculation process, the computer may also execute the first cerebral blood flow-calculation process for obtaining the cerebral blood flow $k_1$ by applying the following formulas (3) or (4):

$$B(t) = k_1 m C_f \int_{t_0}^{t} S(\tau) \cdot e^{-\frac{k_1}{V_d}(t-\tau)} d\tau \quad (3)$$

$$\int_{t_1}^{t_2} B(t) dt = \int_{t_1}^{t_2} k_1 m C_f \int_{t_0}^{t} S(\tau) \cdot e^{-\frac{k_1}{V_d}(t-\tau)} d\tau dt \quad (4)$$

to the obtained first nuclear-medicine-brain-imaging-data, and in the display process, $k_1$ may be displayed in addition to $k_{1d}$.

Furthermore, in the cerebral blood flow-determining method as an exemplary embodiment, the computer may sequentially execute, prior to the above first cerebral blood flow-calculation process, a process for creating a time activity curve that represents temporal changes in counts based on the first nuclear-medicine-brain-imaging-data, a first parameter-calculation process for seeking $k_1 C_f$ and $k_2$ by fitting the following formula (5):

$$B(t) = k_1 C_f \int_{t_0}^{t} S(\tau) \cdot e^{-k_2 \cdot (t-\tau)} d\tau \quad (5)$$

into the obtained time activity curve, a second parameter-calculation process for seeking $C_f V_d$ from the sought $k_1 \cdot C_f$ and $k_2$ based on the following formula (6):

$$k_1 C_f / k_2 = C_f V_d \quad (6)$$

and a third parameter-calculation process for seeking $mC_f$ from the correlation formula expressing the relation between $mC_f$ stored in the database and $C_f V_d$ using the sought $C_f V_d$.

Even in the cerebral blood flow-determining method as an exemplary embodiment, it is possible for the apparatus for determining cerebral blood flow as an exemplary embodiment to comprise various constructions with which it can be provided.

In short, the computer just has to be operated as an apparatus for determining cerebral blood flow of the exemplary embodiment.

Using an apparatus for determining cerebral blood flow, a cerebral blood flow-determining program, and a cerebral blood flow-determining method as an exemplary embodiment, it has become possible in the nuclear medicine brain imaging test under medication to accurately quantify cerebral blood flows of the rest state and the medication state within one day.

DESCRIPTION OF PREFERRED EMBODIMENTS

Figure 1:
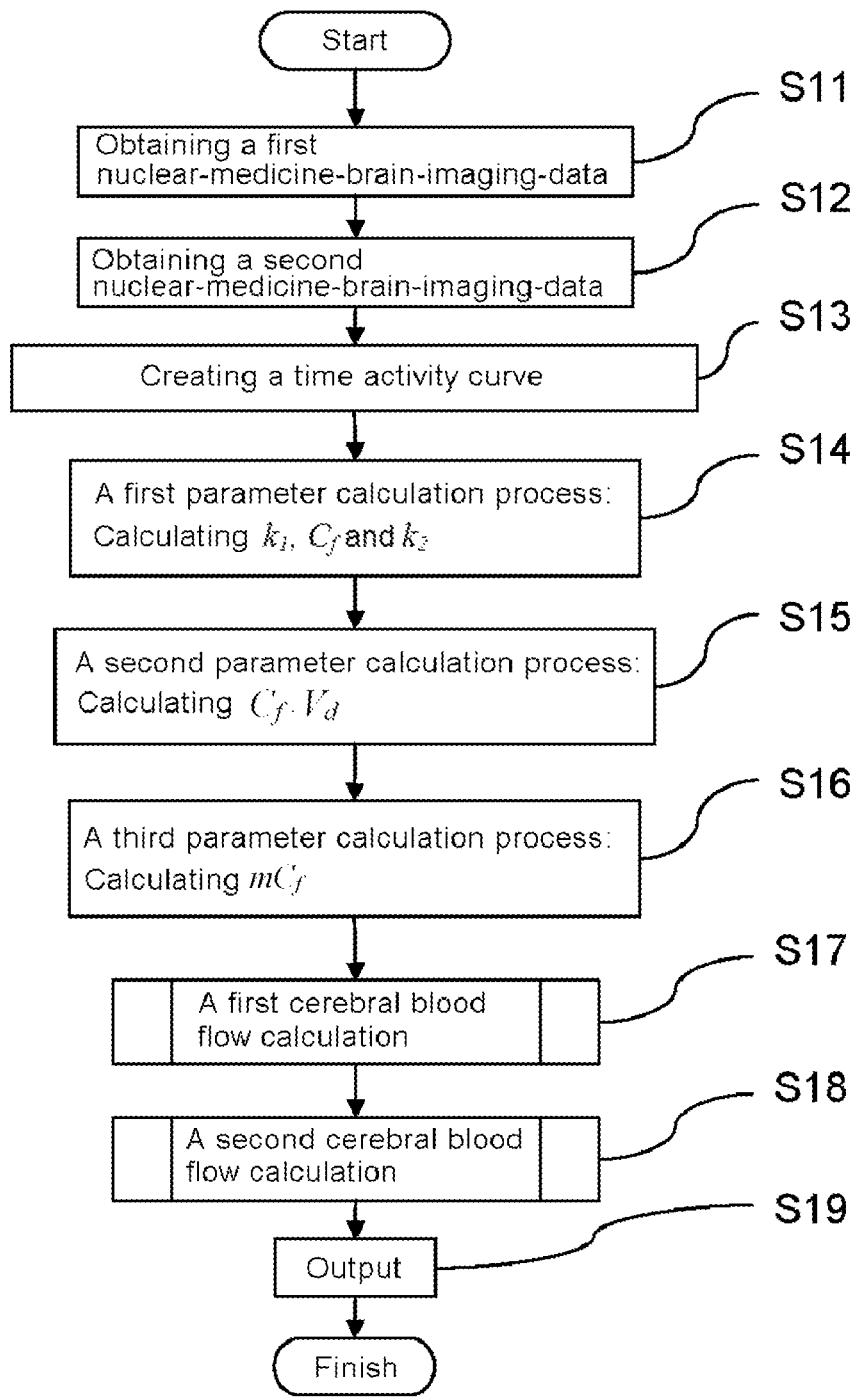
[FIG. 1] is a flow chart showing the outline of a process in a preferred configuration of the apparatus for determining cerebral blood flow as an exemplary embodiment.

Some examples of preferred embodiments of the present invention are presented next.

One exemplary embodiment includes an apparatus for determining cerebral blood flow such as the one in the following. This apparatus comprises a processor and a memory, and wherein the memory storing program instructions causing the apparatus, by being executed by the processor, to:
  obtain second nuclear-medicine-brain-imaging-data resulting from a second radioisotope-drug-injection;
  obtain values required for a formula that is used in the following formulas (1) or (2) among $t_3$ which is the time when the second radioisotope-drug-injection took place (for example, the time when the second radioisotope-drug-injection started), $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;
  obtain, respectively from corresponding storages, a standard input function $S(t)$ which is a function representing temporal changes in inflow of a radioisotope medicine into a standard brain, $mC_f$ which is a scaling factor, $V_d$ which is a cerebral-blood-distribution-coefficient, and $k_1$ which represents the cerebral blood flow generated in a certain cerebral region corresponding to the first radioisotope-drug-injection performed prior to the second radioisotope-drug-injection;
  seek, utilizing the following formulas (1) or (2), $k_{1d}$ which represents cerebral blood flow generated in a certain cerebral region corresponding to the second radioisotope-drug-injection; and $$B_d(t) = k_1 e^{-k_2 t_3} mC_f \int_{t_0}^{t_3} S(\tau) e^{k_2 \tau} d\tau (e^{-k_{2d}(t-t_3)}) + \quad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B_d(t) dt = \quad (2)$$

$$\frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) +$$

$$\int_{t_5}^{t_6} k_{1d} mC_f \int_{t_3}^{t} (S(\tau) + S(\tau - t_3)) \cdot e^{-k_{2d} \cdot (t-\tau)} d\tau dt (t \geq t_3)$$

output the sought cerebral blood flow $k_{1d}$;

wherein $B_d(t)$ in formula (1) or (2) is a radiation count obtained from the second nuclear-medicine-brain-imaging-data and is a radiation count of the certain cerebral region at a time of t, $t_0$ is the time when the first radioisotope-drug-injection took place (for example, the time when the first radioisotope-drug-injection started), $k_2$ is the blood-outflow-rate-constant of brain tissues in the certain cerebral region corresponding to the first radioisotope-drug-injection, where $k_2 = k_1/V_d$, and $k_{2d}$ is the blood-outflow-rate-constant of brain tissues in the certain cerebral region corresponding to the second radioisotope-drug-injection, where $k_{2d} = k_{1d}/V_d$.

According to an embodiment, said memory may store program instructions causing said apparatus, by being executed by the processor, to:
  obtain values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively; and
  seek $k_1$ utilizing the following formulas (3) or (4) and store it in a prescribed storage:

$$B(t) = k_1 mC_f \int_{t_0}^{t} S(\tau) \cdot e^{-\frac{k_1}{V_d} \cdot (t-\tau)} d\tau \quad (3)$$

$$\int_{t_1}^{t_2} B(t) dt = \int_{t_1}^{t_2} k_1 mC_f \int_{t_0}^{t} S(\tau) \cdot e^{-\frac{k_1}{V_d} \cdot (t-\tau)} d\tau dt \quad (4)$$

Where $B(t)$ in formula (3) or (4) is a radiation count obtained from the the nuclear-medicine-brain-imaging-data and is a radiation count of the certain cerebral region at the time of t.

According to an embodiment, said memory may store program instructions causing said apparatus, by being executed by the processor, to:
  create a time activity curve that represents a temporal change in counts, based on the first nuclear-medicine-brain-imaging-data;

seek $k_1C_f$ and $k_2$ by fitting the time activity curve into the following formula (5), and store the sought $k_1C_f$ and $k_2$ in a prescribed storage:

$$B(t) = k_1 C_f \int_{t_0}^{t} S(\tau) \cdot e^{-k_2 \cdot (t-\tau)} d\tau \qquad (5)$$

seek $C_f V_d$ based on the following formula (6) from the sought $k_1C_f$ and $k_2$ and store the sought $C_f V_d$ in a prescribed storage;

$$k_1 C_f / k_2 = C_f V_d \qquad (6)$$

and obtain a correlation formula expressing the relation between $mC_f$ and $C_f V_d$ from a prescribed storage, and seek $mC_f$ by applying the sought $C_f V_d$ to the correlation formula and store the sought $mC_f$ in a prescribed storage. Where $B_W(t)$ in the formula (5) is a radiation count obtained from the first nuclear-medicine-brain-imaging-data and is a radiation count of the second certain cerebral region at the time of t. The cerebral region for obtaining B(t) in the formula (5) may be different from the cerebral region for obtaining B(t) in formulas (1) to (4). For example, the cerebral region for obtaining the B(t) in formula (5) may be the entire brain. Therefore, the cerebral blood flow $k_1$ in formulas (1) to (4) may also be different from the cerebral blood flow $k_1$ in formula (5). The same is true to other portions in the present specifications.

According to an embodiment, the time activity curve may also be created based on images of a portion equivalent to traversal images from the parietal lobe to the cerebellar tent.

According to an embodiment, the correlation formula may also be represented by the following formula (7):

$$mC_f = R \cdot C_f V_d + \alpha \qquad (7)$$

(R: proportional constant, $\alpha$: constant).

According to an embodiment, said memory may store program instructions causing said apparatus, by being executed by the processor, to display the cerebral blood flow $k_1$ and $k_{1d}$ in the certain cerebral region by linking $k_1$ and $k_{1d}$ with the certain cerebral region.

One exemplary embodiment includes a computer readable medium such as the one storing program instructions causing a computer, by being executed by a processor of the computer to:

obtain second nuclear-medicine-brain-imaging-data resulting from a second radioisotope-drug-injection;

obtain values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;

obtain, respectively from corresponding storages, a standard input function S(t) which is a function representing temporal changes in inflow of a radioisotope medicine into a standard brain, $mC_f$ which is a scaling factor, $V_d$ which is a cerebral-blood-distribution-coefficient, and $k_1$ which represents a cerebral blood flow corresponding to a certain cerebral region and to the first radioisotope-drug-injection performed prior to the second radioisotope-drug-injection;

seek $k_{1d}$, which represents cerebral blood flow for the certain cerebral region corresponding to the second nuclear-medicine-brain-imaging-data, utilizing the following formula (1) or (2); and $$B_d(t) = k_1 e^{-k_2 t_3} mC_f \int_{t_0}^{t_3} S(\tau) e^{k_2 \tau} d\tau (e^{-k_{2d}(t-t_3)}) + \\ k_{1d} mC_f \int_{t_3}^{t} (S(\tau) + S(\tau - t_3)) \cdot e^{-k_{2d} \cdot (t-\tau)} d\tau (t \geq t_3) \qquad (1)$$

$$\int_{t_5}^{t_6} B_d(t) dt = \\ \frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) + \\ \int_{t_5}^{t_6} k_{1d} mC_f \int_{t_3}^{t} (S(\tau) + S(\tau - t_3)) \cdot e^{-k_{2d}(t-\tau)} d\tau dt (t \geq t_3) \qquad (2)$$

output the sought cerebral blood flow $k_{1d}$.

Where $B_d(t)$ in formulas (1) or (2) is a radiation count obtained from the second nuclear-medicine-brain-imaging-data and is a radiation count of the certain cerebral region at a time of t, $t_0$ is the time when the first radioisotope-drug-injection took place, $k_2$ is the blood-outflow-rate-constant of brain tissues in the certain cerebral region corresponding to the first radioisotope-drug-injection, where $k_2 = k_1/V_d$, and $k_{2d}$ is the blood-outflow-rate-constant of brain tissues in the certain cerebral region corresponding to the second radioisotope-drug-injection, where $k_{2d} = k_{1d}/V_d$.

According to an embodiment, said computer readable medium may include program instructions causing the computer, by being executed by a processor of the computer to:

obtain values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively; and seek $k_1$ utilizing the following formulas (3) or (4) and store it in a prescribed storage:

$$B(t) = k_1 mC_f \int_{t_0}^{t} S(\tau) \cdot e^{-\frac{k_1}{V_d} \cdot (t-\tau)} d\tau \qquad (3)$$

$$\int_{t_1}^{t_2} B(t) dt = \int_{t_1}^{t_2} k_1 mC_f \int_{t_0}^{t} S(\tau) \cdot e^{-\frac{k_1}{V_d} \cdot (t-\tau)} d\tau dt \qquad (4)$$

Where B(t) in formulas (3) or (4) is a radiation count obtained from the first nuclear-medicine-brain-imaging-data and is a radiation count of the certain cerebral region at the time of t.

One exemplary embodiment includes a computer readable medium such as the one storing program instructions causing a computer, by being executed by a processor of the computer to:

obtain first nuclear-medicine-brain-imaging-data resulting from a first radioisotope-drug-injection and second nuclear-medicine-brain-imaging-data resulting from a second radioisotope-drug-injection;

obtain, respectively from corresponding storages, a standard input function S(t) which is a function representing temporal changes in inflow of a radioisotope medicine into a standard brain, and $V_d$ which is a cerebral-blood-distribution-coefficient;

obtain values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively;

obtain values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;

create a time activity curve representing a temporal change in counts in a first certain cerebral region, based on the first nuclear-medicine-brain-imaging-data;

seek $k_{1W}C_f$ and $k_{2W}$ by fitting the time activity curve into the following formula (5'):

$$B_W(t) = k_{1W}C_f \int_{t_0}^{t} S(\tau) \cdot e^{-k_{2W}\cdot(t-\tau)} d\tau \quad (5')$$

wherein $B_W(t)$ is a radiation count obtained from the first nuclear-medicine-brain-imaging-data and is a radiation count in the first certain cerebral region of a first cerebral region at a time of t, $t_0$ represents the time when the first radioisotope-drug-injection took place, $C_f$ is a scaling factor, $k_{1W}$ represents the cerebral blood flow generated in the first certain cerebral region corresponding to the first radioisotope-drug-injection, and $k_{2W}$ represents the blood-outflow-rate-constant in the first certain cerebral region corresponding to the first radioisotope-drug-injection;

seek $C_f V_d$ based on the following formula (6') from the sought $k_{1W}C_f$ and $k_{2W}$;

$$k_{1W}C_f/k_{2W} = C_f V_d \quad (6')$$

obtain a correlation formula expressing the relation between a scaling factor $mC_f$ and $C_f V_d$ from a prescribed storage, and seek $mC_f$ by applying the sought $C_f \cdot V_d$ to the correlation formula;

seek $k_1$ utilizing the following formulas (3) or (4) using the sought $mC_f$, where $k_1$ represents the cerebral blood flow generated in a second cerebral region corresponding to the first radioisotope-drug-injection;

$$B(t) = k_1 m C_f \int_{t_0}^{t} S(\tau) \cdot e^{-\frac{k_1}{V_d}\cdot(t-\tau)} d\tau \quad (3)$$

$$\int_{t_1}^{t_2} B(t) dt = \int_{t_1}^{t_2} k_1 m C_f \int_{t_0}^{t} S(\tau) \cdot e^{-\frac{k_1}{V_d}\cdot(t-\tau)} d\tau\, dt \quad (4)$$

wherein B(t) is the radiation count obtained from the first nuclear-medicine-brain-imaging-data and is the radiation count of the second cerebral region at a time of t, and $k_2$ is the blood-outflow-rate-constant in the second cerebral region corresponding to the first radioisotope-drug-injection, where $k_2 = k_1/V_d$; and seek $k_{1d}$ which represents the cerebral blood flow generated in the second cerebral region corresponding to the second radioisotope-drug-injection using the sought $k_1$ based on the following formulas (1) or (2):

$$B_d(t) = k_1 e^{-k_2 t_3} m C_f \int_{t_0}^{t_3} S(\tau) e^{k_2 \tau} d\tau (e^{-k_{2d}(t-t_3)}) + \quad (1)$$
$$k_{1d} m C_f \int_{t_3}^{\tau} (S(\tau) + S(\tau - t_3)) \cdot e^{-k_{2d}\cdot(t-\tau)} d\tau (t \geq t_3)$$

$$\int_{t_5}^{t_6} B_d(t) dt = \quad (2)$$
$$\frac{k_1}{k_{2d}} e^{-k_2 t_3} m C_f \int_{t_0}^{t_3} S(\tau) e^{k_2 \tau} d\tau \cdot (e^{-k_{2d}(t_5 - t_3)} - e^{-k_{2d}(t_6 - t_3)}) +$$
$$\int_{t_5}^{t_6} k_{1d} m C_f \int_{t_3}^{\tau} (S(\tau) + S(\tau - t_3)) \cdot e^{-k_{2d}\cdot(t-\tau)} d\tau\, dt (t \geq t_3)$$

wherein $B_d(t)$ is the radiation count obtained from the second nuclear-medicine-brain-imaging-data and is the radiation count of the second cerebral region at a time of t, and $k_{2d}$ is the blood-outflow-rate-constant from the second brain tissues corresponding to the second radioisotope-drug-injection, where $k_{2d} = k_{1d}/V_d$.

One of exemplary embodiments includes a method such as the one for determining cerebral blood flow, including:

obtaining second nuclear-medicine-brain-imaging-data resulting from a second radioisotope-drug-injection;

obtaining values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;

obtaining, respectively from a corresponding storage, a standard input function S(t) which is a function representing temporal changes in inflow of a radioisotope medicine into a standard brain, $mC_f$ which is a scaling factor, $V_d$ which is a cerebral-blood-distribution-coefficient, and $k_1$ which represents the cerebral blood flow generated in a certain cerebral region corresponding to a first radioisotope-drug-injection performed prior to the second radioisotope-drug-injection; and seeking, utilizing the following formulas (1) or (2), $k_{1d}$ which represents the cerebral blood flow generated in a certain cerebral region corresponding to the second radioisotope-drug-injection, $$B_d(t) = k_1 e^{-k_2 t_3} m C_f \int_{t_0}^{t_3} S(\tau) e^{k_2 \tau} d\tau (e^{-k_{2d}(t-t_3)}) + \quad (1)$$
$$k_{1d} m C_f \int_{t_3}^{\tau} (S(\tau) + S(\tau - t_3)) \cdot e^{-k_{2d}\cdot(t-\tau)} d\tau (t \geq t_3)$$

$$\int_{t_5}^{t_6} B_d(t) dt = \quad (2)$$
$$\frac{k_1}{k_{2d}} e^{-k_2 t_3} m C_f \int_{t_0}^{t_3} S(\tau) e^{k_2 \tau} d\tau \cdot (e^{-k_{2d}(t_5 - t_3)} - e^{-k_{2d}(t_6 - t_3)}) +$$
$$\int_{t_5}^{t_6} k_{1d} m C_f \int_{t_3}^{\tau} (S(\tau) + S(\tau - t_3)) \cdot e^{-k_{2d}\cdot(t-\tau)} d\tau\, dt (t \geq t_3)$$

wherein $B_d(t)$ in formulas (1) or (2) is the radiation count obtained from the second nuclear-medicine-brain-imaging-data and is the radiation count of the certain cerebral region at the time of t, $t_0$ is the time when the first radioisotope-drug-injection took place, $k_2$ is the blood-outflow-rate-constant of brain tissues in the certain cerebral region corresponding to the first radioisotope-drug-injection, where $k_2=k_1/V_d$, and $k_{2d}$ is the blood-outflow-rate-constant of brain tissues in the certain cerebral region corresponding to the second radioisotope-drug-injection, where $k_{2d}=k_{1d}/V_d$.

One exemplary embodiment includes a method such as the one for determining cerebral blood flow, including:

obtaining first nuclear-medicine-brain-imaging-data resulting from the first radioisotope-drug-injection and second nuclear-medicine-brain-imaging-data resulting from a second radioisotope-drug-injection;

obtaining, respectively from a corresponding storage, a standard input function S(t) which is a function representing temporal changes in inflow of a radioisotope medicine into a standard brain, $mC_f$ which is a scaling factor, and $V_d$ which is a cerebral-blood-distribution-coefficient;

obtaining values required for a formula that is used in the following formulas (3) or (4) among $t_1$ which is the time when acquisition of the first nuclear-medicine-brain-imaging-data based on the the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively;

obtaining values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;

seeking $k_1$ which represents the cerebral blood flow generated in a certain cerebral region corresponding to the first radioisotope-drug-injection based on the following formulas (3) or (4):

$$B(t) = k_1 mC_f \int_{t_0}^{t} S(\tau) \cdot e^{-\frac{k_1}{V_d}(t-\tau)} d\tau \qquad (3)$$

$$\int_{t_1}^{t_2} B(t)dt = \int_{t_1}^{t_2} k_1 mC_f \int_{t_0}^{t} S(\tau) \cdot e^{-\frac{k_1}{V_d}(t-\tau)} d\tau dt \qquad (4)$$

wherein B(t) is the radiation count obtained from the first nuclear-medicine-brain-imaging-data and is the radiation count of the certain cerebral region at a time of t; and seeking $k_{1d}$ which represents the cerebral blood flow generated in the certain cerebral region corresponding to the second radioisotope-drug-injection using the sought $k_1$, based on the following formulas (1) or (2):

$$B_d(t) = k_1 e^{-k_2 t_3} mC_f \int_{t_0}^{t_3} S(\tau) e^{k_2 \tau} d\tau (e^{-k_{2d}(t-t_3)}) + \qquad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B_d(t)dt = \qquad (2)$$

$$\frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) +$$

$$\int_{t_5}^{t_6} k_{1d} mC_f \int_{t_3}^{t} (S(\tau) + S(\tau - t_3)) \cdot e^{-k_{2d} \cdot (t-\tau)} d\tau dt (t \geq t_3)$$

wherein $B_d(t)$ is the radiation count obtained from the second nuclear-medicine-brain-imaging-data and is the radiation count of the second cerebral region at a time of t, $k_2$ is the blood-outflow-rate-constant of brain tissues in the second cerebral region corresponding to the first radioisotope-drug-injection, where $k_2=k_1/V_d$, and $k_{2d}$ is the blood-outflow-rate-constant of brain tissues in the second cerebral region corresponding to the second radioisotope-drug-injection, where $k_{2d}=k_{1d}/V_d$.

One exemplary embodiment includes a method such as the one for determining cerebral blood flow, including:

obtaining first nuclear-medicine-brain-imaging-data resulting from a first radioisotope-drug-injection and second nuclear-medicine-brain-imaging-data resulting from a second radioisotope-drug-injection;

obtaining, respectively from a corresponding storage, a standard input function S(t) which is a function representing temporal changes in inflow of a radioisotope medicine into a standard brain, and $V_d$ which is a cerebral-blood-distribution-coefficient;

obtaining values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively;

obtaining values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_0$ which is the time when acquisition of the second nuclear-medicine-brain-imaging-data finished, wherein obtaining is conducted by searching within the second nuclear-medicine-brain-imaging-data or by reading out the values from corresponding storages respectively;

creating a time activity curve that represents a temporal change in counts, based on the first nuclear-medicine-brain-imaging-data;

seeking $k_{1W} C_f$ and $k_{2W}$ by fitting the time activity curve into the following formula (5'):

$$B_W(t) = k_{1W} C_f \int_{t_0}^{t} S(\tau) \cdot e^{-k_{2W}(t-\tau)} d\tau \qquad (5')$$

wherein $B_W(t)$ is the radiation count obtained from the first nuclear-medicine-brain-imaging-data and is the radiation count of a first cerebral region at the time of t, $t_0$ represents the time when the first radioisotope-drug-injection took place, $C_f$ is a scaling factor, $k_{1W}$ represents the cerebral blood flow generated in the first certain cerebral region corresponding to the first radioisotope-drug-injection, and $k_{2W}$ represents the blood-outflow-rate-constant in the first certain cerebral region corresponding to the first radioisotope-drug-injection;

seeking $C_f V_d$ based on the following formula (6') from the sought $k_{1W} C_f$ and $k_{2W}$;

$$k_{1W} C_f / k_{2W} = C_f V_2 \quad (6')$$

obtaining a correlation formula expressing the relation between a scaling factor $mC_f$ and $C_f V_d$ from a prescribed storage, and seeking $mC_f$ by applying the sought $C_f V_d$ to the correlation formula;

seeking $k_1$ which represents the cerebral blood flow generated in a second cerebral region corresponding to the first radioisotope-drug-injection using the sought $mC_f$ based on the following formulas (3) or (4):

$$B(t) = k_1 mC_f \int_{t_0}^{t} S(\tau) \cdot e^{-\frac{k_1}{V_d}(t-\tau)} d\tau \quad (3)$$

$$\int_{t_1}^{t_2} B(t) dt = \int_{t_1}^{t_2} k_1 mC_f \int_{t_0}^{t} S(\tau) \cdot e^{-\frac{k_1}{V_d}(t-\tau)} d\tau dt \quad (4)$$

wherein B(t) is a radiation count obtained from the first nuclear-medicine-brain-imaging-data and is a radiation count of the second cerebral region at a time of t; and seeking $k_{1d}$ which represents the cerebral blood flow generated in the second cerebral region corresponding to the second radioisotope-drug-injection using the sought $k_1$ based on the following formulas (1) or (2):

$$B_d(t) = k_1 e^{-k_2 t_3} mC_f \int_{t_0}^{t_3} S(\tau) e^{k_2 \tau} d\tau (e^{-k_{2d}(t-t_3)}) + \\ k_{1d} mC_f \int_{t_3}^{t} (S(\tau) + S(\tau - t_3)) \cdot e^{-k_{2d}(t-\tau)} d\tau (t \geq t_3) \quad (1)$$

$$\int_{t_5}^{t_6} B_d(t) dt = \\ \frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) + \\ \int_{t_5}^{t_6} k_{1d} mC_f \int_{t_3}^{t} (S(\tau) + S(\tau - t_3)) \cdot e^{-k_{2d}(t-\tau)} d\tau dt (t \geq t_3) \quad (2)$$

wherein $B_d(t)$ is the radiation count obtained from the second nuclear-medicine-brain-imaging-data and is the radiation count of the second cerebral region at a time of t, $k_2$ is the blood-outflow-rate-constant of brain tissues in the second cerebral region corresponding to the first radioisotope-drug-injection, where $k_2 = k_1/V_d$, and $k_{2d}$ is the blood-outflow-rate-constant of brain tissues in the second cerebral region corresponding to the second radioisotope-drug-injection, where $k_{2d} = k_{1d}/V_d$.

Each parameter or a function used in the formulas (1) (2) (3) (4) (5) (5') (6) and (6') can be stored in many kinds of storage according to the embodiment. In utilizing these formulas, the processor of an apparatus reads out the necessary parameters or functions from this storage and uses them according to the instructions of a program command. The hardware of the storage can be RAM, ROM, a hard disk or an SSD, and furthermore, it is also possible to use one in which a plurality of hardware are virtually configured as one piece of hardware. Moreover, the construction can also be configured as a primary storage or a secondary storage. In addition, locally installed storage may also be used, but it is also possible to use remote storage that is connected to a network such as Ethernet or Internet. A plurality of the above parameters or functions may also be physically or logically stored in the same storage according to an embodiment, and the parameters or functions may also be physically or logically stored in a different storage accordingly.

Time parameters such as $t_0$, $t_1$, $t_2$, $t_3$, $t_5$, and $t_6$ etc. may also be saved in a predetermined storage by an apparatus that acquires a radioisotope-drug-injection or brain nuclear medicine data by automatically recording these times in accordance with the start of injection of a drug or the start or the finish of data collection. The exemplary embodiment may also be configured by reading out time parameters from the storage so as to be applied to (1) to (6').

Utilizing the formulas (1) to (6') does not only mean algebraically solving these formulas. For example, this may also mean being used for numerical analysis. For example, the purpose of formulas (1) or (2) is to seek $k_{1d}$. However, this does not have to be achieved by solving the formulas (1) or (2) for $k_{1d}$, but may also be approximately achieved using a method of numerical analysis. The same is true with regard to other formulas.

It should be noted that embodiments in the present invention are not restricted to using formulas (1) to (6') in a form that has been described in the present specifications. For example, the embodiments are not limited to a construction in which formulas (1) to (6') are implemented in program instructions in a form that is described in the present specifications. For example, as described above, because there is a relationship such as $k_2 = k_1/V_d$, $k_{2d} = k_{1d}/V_d$, formulas (1) to (6') may be modified so as not to include $k_2$ or $k_{2d}$. Furthermore, it would be easy for those in the industry to modify formulas (1) to (6') by moving a desired term to the left side or the right side, or to the denominator or the numerator. Furthermore, a specified term in the formula may also be calculated by a process that is different from the other terms in the same formula. These embodiments are also included in the scope of the present invention. Therefore, each embodiment described in the claims shall be understood as including all embodiments in which the formulas described in the claims are principally used. Hereinafter, preferred embodiments in the present invention are described in greater detail with reference to figures. However, it should be noted that the following explanations are basically examples of preferred embodiments and are not intended to limit the scope of the present invention.

[A Process by an Apparatus for Determining Cerebral Blood Flow]

FIG. 1 is a drawing showing the outline of the process of an apparatus for determining cerebral blood flow 10 which is an exemplary embodiment. By operating the apparatus 10, it is possible to realize a cerebral blood flow-determining method which is also an exemplary embodiment. It should be noted that the scaling factor $mC_f$ is estimated based on a time activity curve in the disclosed example, but it is also possible to use the $mC_f$ that is obtained by a publically known method based on sampling data from the arterial blood of a subject (for example, a method stated in a document (Hidehiro Iida et al, The Journal of Nuclear Medicine, December 1994, Vol. 35, No. 12, pp 2019-2030).

The apparatus 10 first acquires a plurality of sets of temporally consecutive nuclear-medicine-brain-imaging-data, following a first radioisotope-drug-injection (step S11). In one preferred embodiment, the sets of the nuclear-medicine-brain-imaging-data acquired herein are used for creating a time activity curve to be described later and also used as the first nuclear-medicine-brain-imaging-data for determining the amount of cerebral blood flow. In the present example, the nuclear-medicine-brain-imaging-data at each point of time comprises a plurality of spatially consecutive tomographic images (preferably traversal images). In spite of SPECT data, it is possible to use PET data as the nuclear-medicine-brain-imaging-data.

Once acquiring the sets of first nuclear-medicine-brain-imaging-data, a second radioisotope-drug-injection takes place to obtain a second nuclear-medicine-brain-imaging-data (step S12). Herein, in case of performing medication, a drug with vasodilator action such as acetazolamide etc. is administered prior to performing the second radioisotope-drug-injection and after the first nuclear-medicine-brain-imaging-data is acquired. It should be noted that the second nuclear medicine image data in this case may be obtained as a plurality of temporally consecutive nuclear-medicine-brain-imaging-data, obtained in the same procedure as the acquisition of the above first nuclear medicine image data.

Next, the apparatus 10 uses the acquired nuclear-medicine-brain-imaging-data and creates a time activity curve (step S13). The time activity curve is a curve line representing temporal changes in counts and may be acquired by plotting counts with respect to the elapsed times after administering a radioisotope medicine. For creating the time activity curve, it is necessary to extract pixels corresponding to the site into which the radioisotope medicine has been taken. The extraction of the pixels may be conducted by various methods. For example, for nuclear-medicine-brain-imaging-data at each point of time, threshold values may be set based on the maximum value and the minimum value of counts, which will then be regarded as the upper limit and the lower limit. For example, a count that is 30% smaller than the maximum value and a count that is 10% greater than the minimum value is respectively regarded as the threshold value of the upper limit and the lower limit. Subsequently, counts greater than the threshold value based on the maximum value and the counts smaller than the threshold value based on the minimum value are to be cut off. And it makes possible to extract the remaining pixels as pixels to be used for creation of the time activity curve.

The time activity curve may be obtained by calculating the average value of the counts of the pixels that have been extracted at each point of time and plotting with respect to the elapsed time after a radioisotope medicine is administered.

The apparatus 10 obtains $k_1 C_f$ and $k_2$ by fitting the following formula (5):

$$B(t) = k_1 C_f \int_{t_0}^{t} S(\tau) \cdot e^{-k_2 \cdot (t-\tau)} d\tau \quad (5)$$

into the time activity curve that has been created above (step S14).

In step S15, the apparatus 10 obtains $C_f V_d$ from the $k_1 C_f$ and $k_2$ calculated above, based on the following formula (6):

$$k_1 C_f / k_2 = C_f V_d \quad (6)$$

and reads out, from a database 30, a correlation formula expressing the relation between $mC_f$ and $C_f V_d$ to obtain the $mC_f$ by applying the above $C_f V_d$ to the correlation formula (step S16).

Next, the apparatus 10 reads out a standard input function S(t) from the database 30 and applies the following formulas (3) or (4):

$$B(t) = k_1 m C_f \int_{t_0}^{t} S(\tau) \cdot e^{-\frac{k_1}{V_d}(t-\tau)} d\tau \quad (3)$$

$$\int_{t_1}^{t_2} B(t) dt = \int_{t_1}^{t_2} k_1 m C_f \int_{t_0}^{t} S(\tau) \cdot e^{-\frac{k_1}{V_d}(t-\tau)} d\tau dt \quad (4)$$

to the above sought $mC_f$ and the first nuclear-medicine-brain-imaging-data so as to obtain the cerebral blood flow $k_1$ per unit region based on the first nuclear-medicine-brain-imaging-data (step S17).

Figure 2:
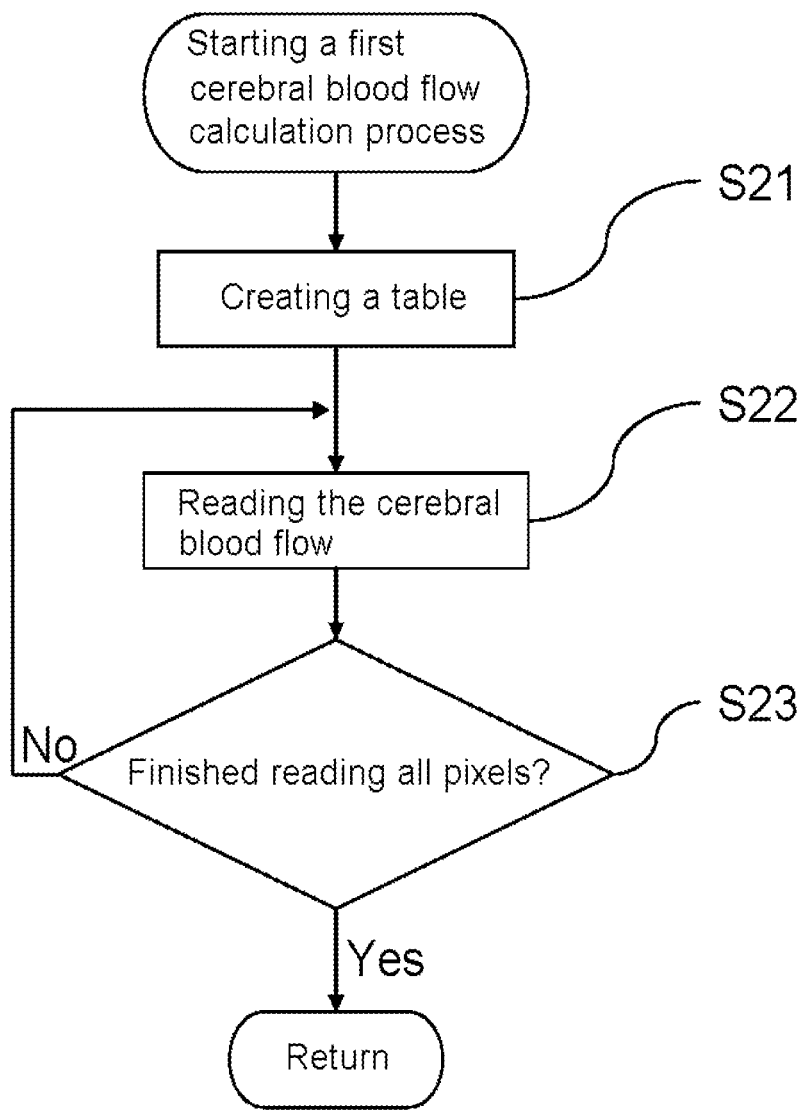
[FIG. 2] is a flow chart showing the outline of a process in a preferred configuration of the apparatus for determining cerebral blood flow (a portion involving the first cerebral blood flow-calculation part) as an exemplary embodiment.

FIG. 2 is a drawing showing the flow of processes for calculating cerebral blood flow based on the first nuclear-medicine-brain-imaging-data (step S17, hereinafter referred to as the "first cerebral-blood-flow-calculation-step"). By substituting $mC_f$ and the standard input function S(t) read out from the database 30 for the above formulas (3) or (4), the apparatus 10 creates a table representing the cerebral blood flow $k_1$ corresponding to the count (B(t) (for determining the cerebral blood flow utilizing formula (3)) or to the left side of the above formula (4) (for determining the cerebral blood flow utilizing formula (4)) (step S21).

The table can be created by using a publicly known method. For example, a method that can be used is to obtain a cerebral blood flow $k_1$ by means of fitting corresponding to all counts from the minimum count to the maximum count of all the pixels in a nuclear-medicine-brain-image used for quantification, and put the same together as a table. The value of a distribution coefficient $V_d$ can be a value preliminarily determined by a publicly known method, and may be substituted for the above formula (3) or (4). Thereby, the number of parameters used for the fitting may be reduced, making it possible to improve the calculation accuracy of $k_1$.

It should be noted that a plurality of temporally consecutive images may be selected from the first nuclear-medicine-brain-imaging-data obtained in the above step S11 and be used as nuclear-medicine-brain-images to be used for the calculation of cerebral blood flow. For example, in a case of calculation based on the above formula (3), the radiation count B(t) is obtained by summing counts over every point of time for every pixel in the selected image. The acquisition time of the image data t is the time falling in the middle of the earliest imaging time and the latest imaging time among times for acquiring the series of selected images. For example, among a series of image data obtained via acquisition of 15 phases when one phase is two minutes, if data from 6 to 15 phases is used for determination, the data acquisition time t is used as 20 minutes for the calculation.

The apparatus 10 reads out, from the table, the value of the cerebral blood flow $k_1$ corresponding to the count B(t) obtained in each pixel (step S22). The apparatus 10 also determines whether or not the determining process of the cerebral blood flow $k_1$ has been conducted for all the pixels for which the cerebral blood flow $k_1$ was obtained (step S23), if not finished for all the pixels (No in step S23), the determining process is performed for the remaining pixels (step S22). When the determining process is completed for all the pixels (Yes in step S23), the cerebral blood flow calculation process is completed.

In the present example, the cerebral blood flow $k_1$ is read out from the created table. But of course it is possible to employ other methods. For example, instead of creating the above table, the cerebral blood flow $k_1$ corresponding to the count may be obtained through fitting for the entire region for which it is desired to obtain the cerebral blood flow $k_1$.

When the first cerebral-blood-flow-calculation-step is completed, the apparatus 10 applies the following formulas (1) or (2):

$$B_d(t) = k_1 e^{-k_2 t_3} mC_f \int_{t_0}^{t_3} S(\tau) e^{k_2 \tau} d\tau (e^{-k_{2d}(t-t_3)}) + \quad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B_d(t) dt = \quad (2)$$

$$\frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) +$$

$$\int_{t_5}^{t_6} k_{1d} mC_f \int_{t_3}^{t} (S(\tau) + S(\tau - t_3)) \cdot e^{-k_{2d} \cdot (t-\tau)} d\tau dt (t \geq t_3)$$

to the $mC_f$ and the second nuclear-medicine-brain-imaging-data to obtain a cerebral blood flow $k_{1d}$ per unit region based on the second nuclear-medicine-brain-imaging-data (step S18, hereinafter, referred to as the "second cerebral-blood-flow-calculation-step")

In the second cerebral-blood-flow-calculation-step (step S18), the point of using the above formulas (1) or (2) is the most characteristic part. While the influence from the remaining radiation by a radioisotope drug administered in the first radioisotope-drug-injection is taken into consideration in the first term on the right side in the formulas (1) and (2), consideration is also given to the remaining amount of the radioisotope drug administered in the first radioisotope-drug-injection with regard to the form of the standard input function. Using either formulas (3) or (4) until the second radioisotope-drug-injection time $t_3$ and using either formulas (1) or (2) after the $t_3$, the cerebral blood flow in the rest state and the cerebral blood flow under medication may accurately be obtained in a single day test for determining the amount of cerebral blood flow.

In a preferred embodiment, the time $t_1$ and $t_2$ are determined as image information data such as DICOM tag information (if saved in a DICOM format) based on information to be taken into a computer together with acquired image data. For example, in normal nuclear medicine image diagnosis apparatus, a time of starting acquisition of imaging data and a time of finishing acquisition of imaging data are stored and linked with image data, and the data is taken into a computer simultaneously when the computer obtains the image data. Moreover, if the time of administering the radioisotope medicine that has been input separately by a user, is used, the time $t_1$ and $t_2$ may easily be calculated. The input of the time of injection of the radioisotope medicine by the user may be conducted directly on the user interface of a computer that performs the calculation of cerebral blood flow according to the exemplary embodiment. But they may also be input on the user interface in a nuclear medicine image diagnosis apparatus that has performed imaging. If the time is input on the user interface in the nuclear medicine image diagnosis apparatus, the information regarding the time may be taken into a computer as image information data at the same time as the image data together with the acquisition start time, finish time, etc.

Furthermore, in some cases, acquisition of imaging data starts at the same time as injection of a radioisotope medicine. In such a case, the $t_1$ and $t_2$ may be directly obtained from the start time and the finish time of the acquisition.

It should be noted that $t_1$ and $t_2$ may, of course, be input directly by the user on the user interface of a computer that executes a method which is an exemplary embodiment.

Thus far, a way for obtaining parameters by a computer has been described by taking $t_1$ and $t_2$ as an example, but other parameters, e.g. $t_0$, $t_3$, $t_5$, and $t_6$, may also be taken into a computer in similar manner.

Figure 3:
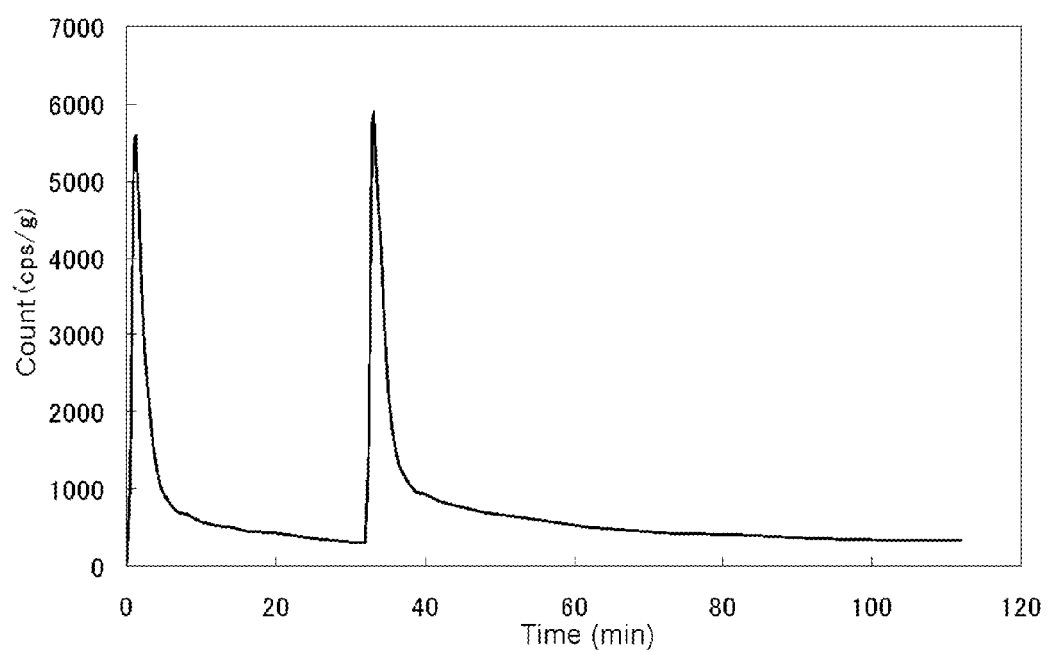
[FIG. 3] is a drawing showing one example of a standard input function in the present invention.

FIG. 3 is one example of a standard input function for a test under medication. In the embodiment, a standard input function until the second radioisotope-drug-injection ($t \leq t_3$) is S(t) and a standard input function after the second radioisotope-drug-injection is (S(t)+S(t–$t_3$)). As described, after the second radioisotope-drug-injection, that is $t \geq t_3$, the input by the second radioisotope-drug-injection ends up being added to the input based on the first radioisotope-drug-injection.

Figure 4:
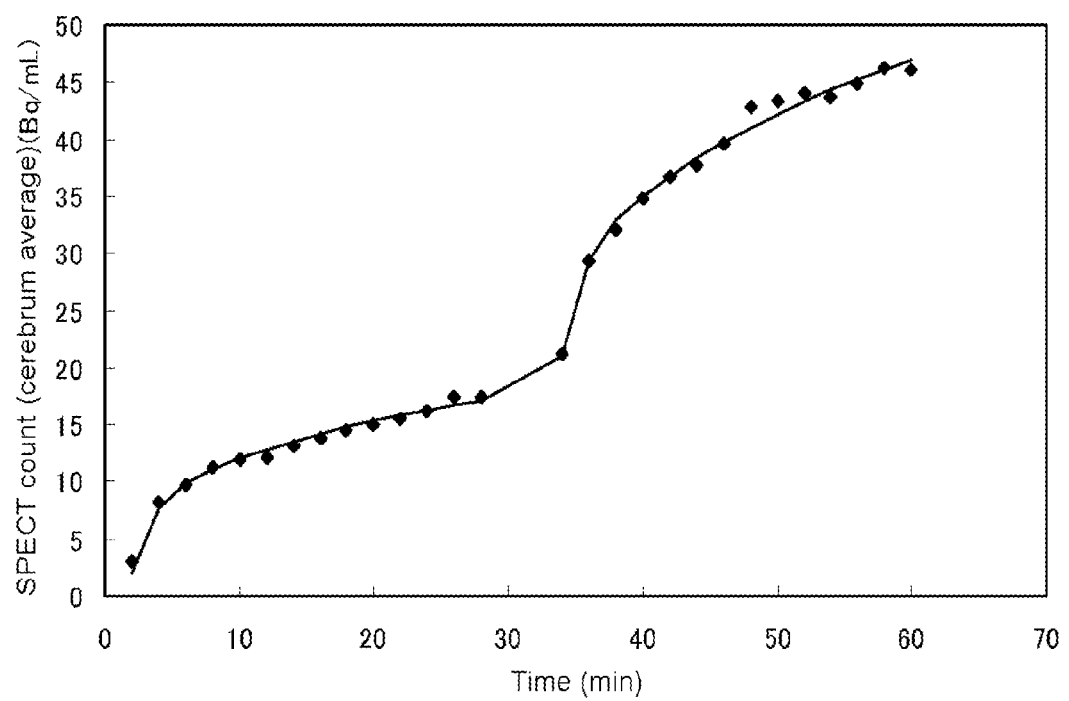
[FIG. 4] is a drawing showing one example of a time activity curve in a test under medication.

FIG. 4 is one example of data showing the temporal changes in SPECT count for the case of performing a test under medication, and points therein are actual measurement values. In FIG. 4, the results of fitting using the above formulas (4) and (2) are indicated by a solid line respectively before the second radioisotope-drug-injection ($t \leq t_3$) and after the second radioisotope-drug-injection ($t \geq t_3$). The actual measurement values and the calculated values show an extremely favorable match. As described, it is shown that the formulas used in the embodiments can give results to which the actual data has been favorably reflected.

Figure 5:
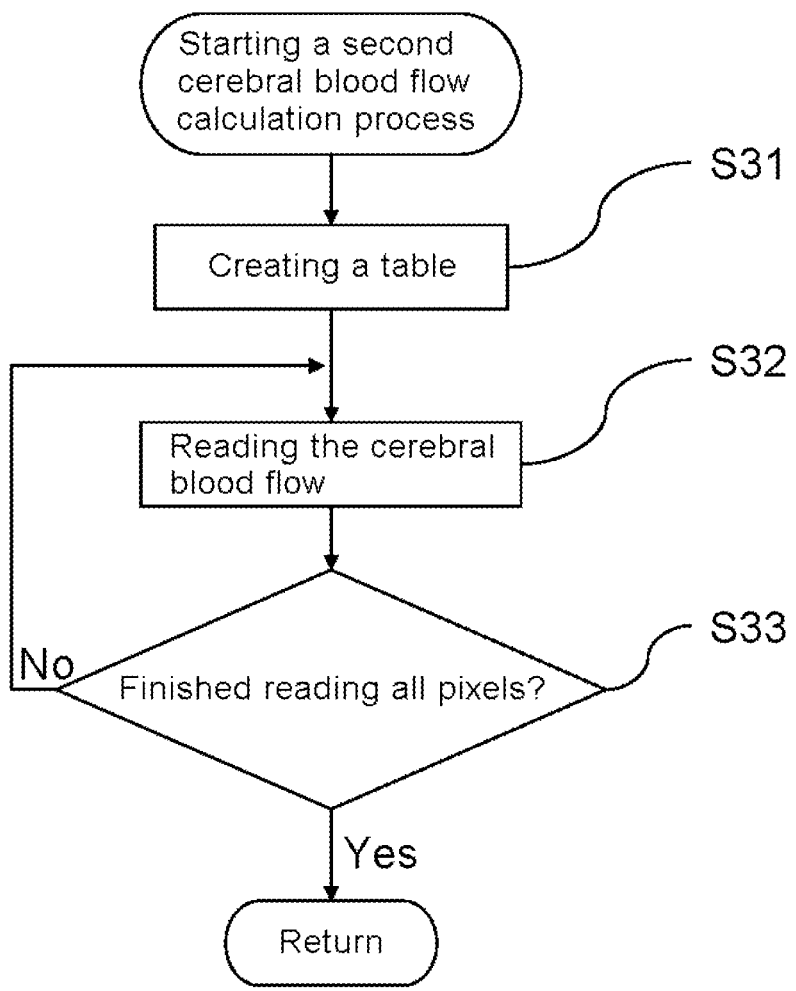
[FIG. 5] is a flow chart showing the outline of a process in a preferred configuration of the apparatus for determining cerebral blood flow (a portion involving the second cerebral blood flow-calculation part) as an exemplary embodiment.

A flow chart showing a flow of processes in the second cerebral-blood-flow-calculation-step (step S18) is shown in FIG. 5. Even in the second cerebral-blood-flow-calculation-step, as in the first cerebral-blood-flow-calculation-step, a step for creating a table (step S31) and a step for reading out cerebral blood flow (step S32) are executed with regard to all pixels.

The apparatus 10 outputs the sought cerebral blood flow $k_1$ and $k_{1d}$ by an outputting device such as a display (step S19). The output may be conducted by various forms. For example, if $k_1$ (sought for each pixel in the first nuclear-medicine-brain-image) is taken as an example, it is possible to display the values of the cerebral blood flow $k_1$ on the corresponding pixels by a luminance or a color in dependence of the determined value of the cerebral flow. It is also possible to represent position of each pixel with a numerical value such as a coordinate etc., and display the cerebral blood flow $k_1$ as a numerical value so as to correspond to the former numerical value.

[Construction of an Apparatus for Determining Cerebral Blood Flow]

Figure 6:
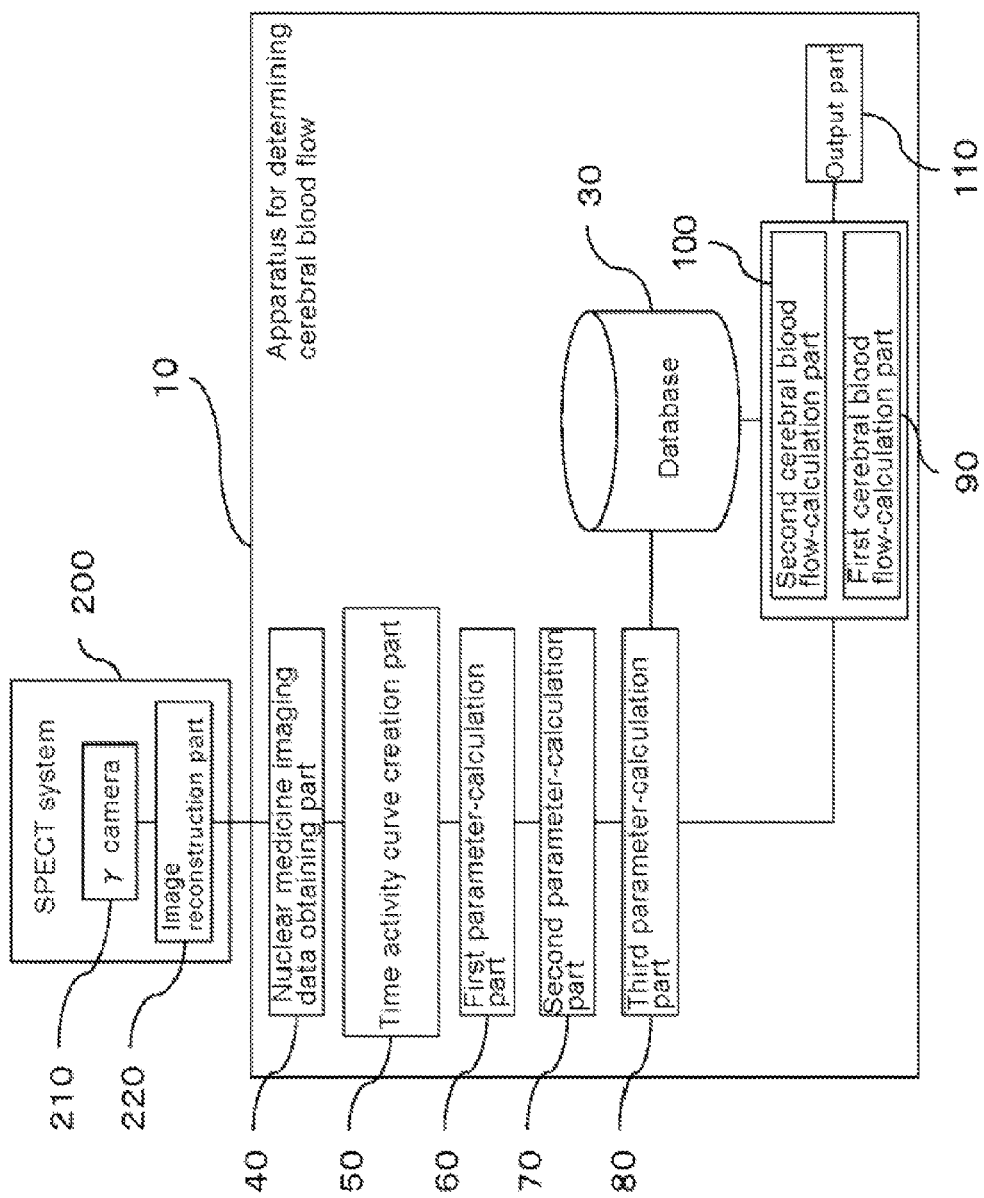
[FIG. 6] is a functional block diagram in a preferred configuration of the apparatus for determining cerebral blood flow as an exemplary embodiment.

FIG. 6 is a drawing showing a construction in the most preferred configuration of the apparatus for determining cerebral blood flow 10. This apparatus may be configured as a computer in which a cerebral blood flow-determining program 300 to be described later has been read.

It should be noted that in the present embodiment, a SPECT image is used as a nuclear-medicine-brain-image but it is not limited to this. In the present embodiment, other nuclear medicine brain imaging such as PET images, planar images, etc. may be subjected in spite of SPECT images.

In a preferred configuration, the apparatus 10 comprises a database 30, a nuclear medicine image data-obtaining part 40, a time activity curve-creation part 50, a first parameter-calculation part 60, a second parameter-calculation part 70, a third parameter-calculation part 80, a first cerebral blood flow-calculation part 90, a second cerebral blood flow-calculation part 100, and an output part 110. In a preferred configuration, the apparatus 10 is connected to a SPECT system 200 via an electric communication line, and the SPECT system 200 comprises a γ camera 210 and an image reconstruction part 220. In this example, projection data acquired by the γ camera 210 is reconstructed into a series of tomographic images by the image reconstruction part 220.

Figure 7:
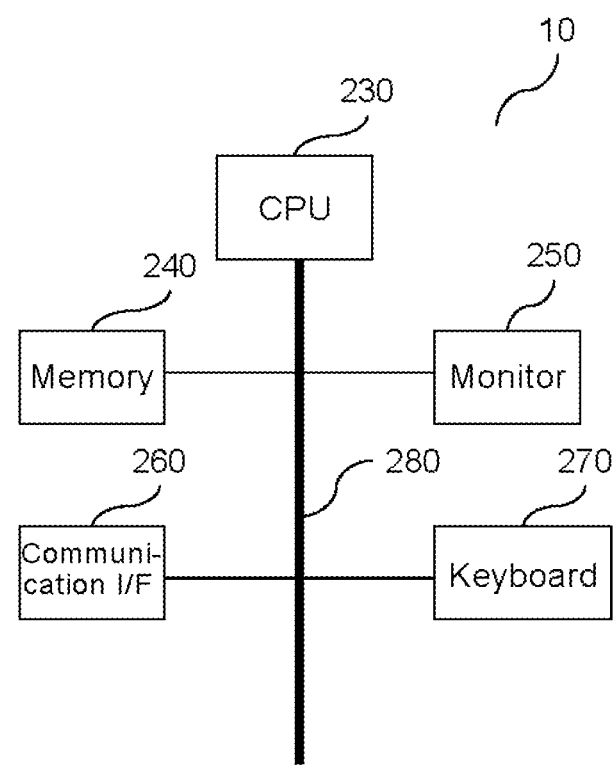
[FIG. 7] is a drawing showing a system construction in a preferred configuration of the apparatus for determining cerebral blood flow as an exemplary embodiment.

FIG. 7 is a system construction in the most preferred configuration of the apparatus 10. In the most preferred configuration of the apparatus 10, a CPU 230, a memory 240, and an output device such as a monitor 250, a communication interface 260, and an input device 270 such as a keyboard are connected via a bus 280. In addition to this, the apparatus 10 may also comprise a CD-ROM drive, an USB interface, etc. The communication interface 260 is used to connect with the SPECT system 200. Furthermore, the cerebral blood flow-determining program 300 is stored in the memory 240.

In a preferred configuration, the database 30 stores at least a correlation formula expressing the relationship between $mC_f$ and $C_r \cdot V_d$, and a standard input function. The standard input function obtained by a publicly known method (for example, the method explained in a document (Hidehiro Iida et al, The Journal of Nuclear Medicine, December 1994, Vol. 35, No. 12, pp 2019-2030)) may be used. The correlation formula expressing $mC_f$ and $C_f V_d$ may be obtained by seeking $mC_f$ and $C_f V_d$ in a plurality of subjects and linearly approximating a graph in which $mC_f$ has been plotted. The $mC_f$ may be obtained by a publicly known method using sampling data of arterial blood, and $C_f V_d$ may be obtained by fitting a time activity curve into a two-compartment model formula.

The nuclear medicine image data-obtaining part 40 performs processes involving the above step S11 and step S12. Specifically, a plurality of temporally consecutive nuclear-medicine-brain-imaging-data (the first nuclear-medicine-brain-imaging-data and the second nuclear-medicine-brain-imaging-data) is acquired by a SPECT system. The first nuclear-medicine-brain-imaging-data acquired herein is used for creating a time activity curve as well as for determining the amount of cerebral blood flow. In the present example, the nuclear medicine image data at each temporal point comprises a plurality of spatially consecutive tomographic images (preferably transversal images).

The time activity curve-creation part 50 performs a process involving the above step S13.

The first parameter-calculation part 60 performs a process involving the above step S14.

The second parameter-calculation part 70 performs a process involving the above step S15.

The third parameter-calculation part 80 performs a process involving the above step S16.

The first cerebral blood flow-calculation part 90 performs a process involving the above step S17 as well as steps S21 to 23.

The second cerebral blood flow-calculation part 100 performs a process involving the above step S18 as well as steps S31 to 33.

The output part 110 performs a process involving the above step S19.

Thus far, the most preferred configuration of the apparatus 10 has been described.

Next, the cerebral blood flow-determining program 300 is described as an exemplary embodiment. As described above, the apparatus 10 may be configured as a computer in which the cerebral blood flow-determining program 300 has been read.

Figure 8:
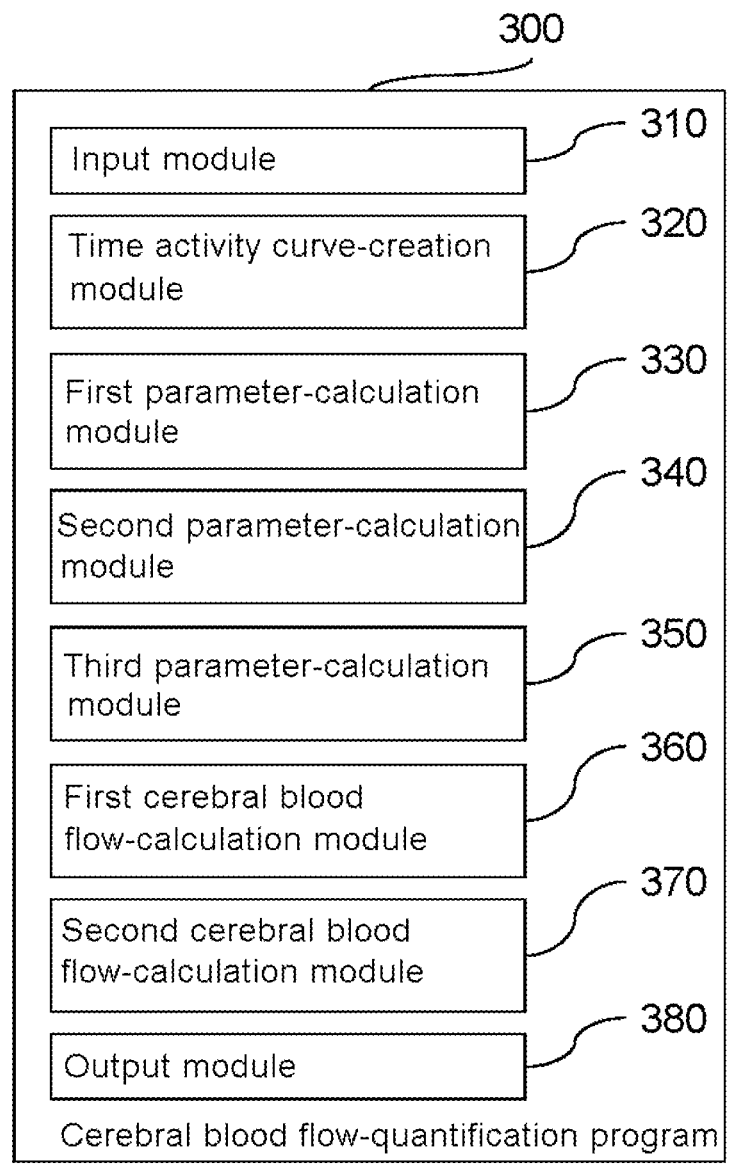
[FIG. 8] is a drawing showing a construction in a preferred configuration of the cerebral blood flow-determining program as an exemplary embodiment.

FIG. 8 is a drawing showing a construction of a cerebral blood flow-determining program in the most preferred configuration. In the most preferred configuration, the cerebral blood flow-determining program 300 comprises an input module 310, a time activity curve-creation module 320, a first parameter-calculation module 330, a second parameter-calculation module 340, a third parameter-calculation module 350, a first cerebral blood flow-calculation module 360, a second cerebral blood flow-calculation module 370, and an output module 380.

The input module 310 causes the computer to perform processes involving step S11 and step S12.

The time activity curve-creation module 320 causes the computer to perform processes involving step S13.

The first parameter-calculation module 330 causes the computer to perform processes involving step S14.

The second parameter-calculation module 340 causes the computer to perform processes involving step S15.

The third parameter-calculation module 350 causes the computer to perform processes involving step S16.

The first cerebral blood flow-calculation module 360 causes the computer to perform processes involving step S17 as well as steps S21 to 23.

The second cerebral blood flow-calculation module 370 causes the computer to perform processes involving step S18 as well as steps S31 to 33.

The output module 380 causes the computer to perform processes involving step S19.

The present invention may be utilized, for example, in a field of image processing programs.

The present invention may be implemented in various forms, and there are a large number of variations in addition to those presented as examples of the embodiment of the present invention. Individual features included in various implemented examples that have been described are not limited to usage with implemented examples in which these features are directly explained to be included, but may be used in combination with other examples that are not described herein or various specific examples that have not been described. It should be noted that these variations are all included in the scope of the present invention and the applicant claims to possess the right to have the patent granted regardless of whether or not a patent is claimed in the current set of attached Claims.

What is claimed:

1. An apparatus for determining cerebral blood flow, comprising a processor and a memory, wherein the memory storing program instructions causing the apparatus, by being executed by the processor, to:

obtain second nuclear-medicine-brain-imaging-data resulting from a second radioisotope-drug-injection;

obtain values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;

obtain, respectively from corresponding storages, a standard input function S(t) which is a function representing temporal changes in inflow of a radioisotope medicine into a standard brain, $mC_f$ which is a scaling factor, $V_d$ which is a cerebral-blood-distribution-coefficient, and $k_1$ which represents the cerebral blood flow generated in a certain cerebral region corresponding to the first radioisotope-drug-injection performed prior to the second radioisotope-drug-injection;

seek, utilizing the following formula (1) or (2), $k_{1d}$ which represents cerebral blood flow generated in a certain cerebral region corresponding to the second radioisotope-drug-injection; and $$B_d(t) = k_1 e^{-k_2 t_3} mC_f \int_{t_0}^{t_3} S(\tau) e^{k_2 \tau} d\tau (e^{-k_{2d}(t-t_3)}) + \quad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B_d(t) dt = \quad (2)$$

$$\frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) +$$

$$\int_{t_5}^{t_6} k_{1d} mC_f \int_{t_3}^{t} (S(\tau) + S(\tau - t_3)) \cdot e^{-k_{2d} \cdot (t-\tau)} d\tau dt (t \geq t_3)$$

output the sought cerebral blood flow $k_{1d}$;

wherein $B_d(t)$ in formula (1) or (2) is a radiation count obtained from the second nuclear-medicine-brain-imaging-data and is a radiation count of the certain cerebral region at a time of t, $t_0$ is the time when the first radioisotope-drug-injection took place, $k_2$ is the blood-outflow-rate-constant of brain tissues in the certain cerebral region corresponding to a first radioisotope-drug-injection, where $k_2 = k_1/V_d$, and $k_{2d}$ is the blood-outflow-rate-constant of brain tissues in the certain cerebral region corresponding to the second radioisotope-drug-injection, where $k_{2d} = k_{1d}/V_d$.

2. The apparatus according to claim 1, wherein the memory storing program instructions causing the apparatus, by being executed by the processor, to:

obtain values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively; and seek $k_1$ utilizing the following formulas (3) or (4) and store it in a prescribed storage:

$$B(t) = k_1 mC_f \int_{t_0}^{t} S(\tau) \cdot e^{-\frac{k_1}{V_d} \cdot (t-\tau)} d\tau \quad (3)$$

$$\int_{t_1}^{t_2} B(t) dt = \int_{t_1}^{t_2} k_1 mC_f \int_{t_0}^{t} S(\tau) \cdot e^{-\frac{k_1}{V_d} \cdot (t-\tau)} d\tau dt \quad (4)$$

wherein B(t) in formula (3) or (4) is a radiation count obtained from the nuclear-medicine-brain-imaging-data and is a radiation count of the certain cerebral region at the time of t.

3. The apparatus according to claim 1, wherein the memory storing program instructions causing the apparatus, by being executed by the processor, to:

create a time activity curve that represents a temporal change in counts, based on the first nuclear-medicine-brain-imaging-data;

seek $k_1 C_f$ and $k_2$ by fitting the time activity curve into the following formula (5), and store the sought $k_1 C_f$ and $k_2$ in a prescribed storage;

$$B(t) = k_1 C_f \int_{t_0}^{t} S(\tau) \cdot e^{-k_2 \cdot (t-\tau)} d\tau \quad (5)$$

seek $C_f V_d$ based on the following formula (6) from the sought $k_1 C_f$ and $k_2$ and store the sought $C_f V_d$ in a prescribed storage;

$$k_1 C_f / k_2 = C_f V_d \quad (6)$$

and obtain a correlation formula expressing the relation between $mC_f$ and $C_f V_d$ from a prescribed storage, and seek $mC_f$ by applying the sought $C_f V_d$ to the correlation formula and store the sought $mC_f$ in a prescribed storage, wherein $B_H(t)$ in the formula (5) is a radiation count obtained from the first nuclear-medicine-brain-imaging-data and is a radiation count of the second certain cerebral region at the time of t.

4. The apparatus according to claim 3, wherein the time activity curve is created based on images of a portion equivalent to traversal images from the parietal lobe to the cerebellar tent.

5. The apparatus according to claim 3, wherein the correlation formula is represented by the following formula (7):

$$mC_f = R \cdot C_f V_d + \alpha \quad (7)$$

(R: proportional constant, $\alpha$: constant).

6. The apparatus according to claim 1, wherein the memory stores program instructions causing the apparatus, by being executed by the processor, to display the cerebral blood flow $k_1$ and $k_{1d}$ in the certain cerebral region by linking $k_1$ and $k_{1d}$ with the certain cerebral region.

7. A non-transitory computer readable medium for storing program instructions, wherein the computer readable medium includes program instructions causing a computer, by being executed by a processor of the computer to:

obtain second nuclear-medicine-brain-imaging-data resulting from a second radioisotope-drug-injection;

obtain values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;

obtain, respectively from corresponding storages, a standard input function S(t) which is a function representing temporal changes in inflow of a radioisotope medicine into a standard brain, $mC_f$ which is a scaling factor, $V_d$ which is a cerebral-blood-distribution-coefficient, and $k_1$ which represents a cerebral blood flow corresponding to a certain cerebral region and to the first radioisotope-drug-injection performed prior to the second radioisotope-drug-injection;

seek, utilizing the following formula (1) or (2), $k_{1d}$ which represents cerebral blood flow for the certain cerebral region corresponding to the second nuclear-medicine-brain-imaging-data; and $$B_d(t) = k_1 e^{-k_2 t_3} mC_f \int_{t_0}^{t_3} S(\tau) e^{k_2 \tau} d\tau (e^{-k_{2d}(t-t_3)}) + \quad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

-continued $$\int_{t_5}^{t_6} B_d(t)dt = \tag{2}$$

$$\frac{k_1}{k_{2d}} e^{-k_2 t_3} mC_f \int_{t_0}^{t_3} S(\tau) e^{k_2 \tau} d\tau \cdot (e^{-k_{2d}(t_5 - t_3)} - e^{-k_{2d}(t_6 - t_3)}) +$$

$$\int_{t_5}^{t_6} k_{1d} mC_f \int_{t_3}^{t} (S(\tau) + S(\tau - t_3)) \cdot e^{-k_{2d} \cdot (t - \tau)} d\tau dt (t \geq t_3)$$

output the sought cerebral blood flow $k_{1d}$,
wherein $B_d(t)$ in formulas (1) or (2) is a radiation count obtained from the second nuclear-medicine-brain-imaging-data and is a radiation count of the certain cerebral region at a time of t, $t_0$ is the time when the first radioisotope-drug-injection took place, $k_2$ is the blood-outflow-rate-constant of brain tissues in the certain cerebral region corresponding to a first radioisotope-drug-injection, where $k_2 = k_1/V_d$, and $k_{2d}$ is the blood-outflow-rate-constant of brain tissues in the certain cerebral region corresponding to the second radioisotope-drug-injection, where $k_{2d} = k_{1d}/V_d$.

8. The computer readable medium according to claim 7, wherein the computer readable medium includes program instructions causing the computer, by being executed by a processor of the computer to:
   obtain values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively; and
   seek $k_1$ utilizing the following formulas (3) or (4) and store it in a prescribed storage;

$$B(t) = k_1 mC_f \int_{t_0}^{t} S(\tau) \cdot e^{-\frac{k_1}{V_d}(t-\tau)} d\tau \tag{3}$$

$$\int_{t_1}^{t_2} B(t)dt = \int_{t_1}^{t_2} k_1 mC_f \int_{t_0}^{t} S(\tau) \cdot e^{-\frac{k_1}{V_d}(t-\tau)} d\tau dt \tag{4}$$

wherein B(t) in formulas (3) or (4) is a radiation count obtained from the first nuclear-medicine-brain-imaging-data and is a radiation count of the certain cerebral region at the time of t.

9. A non-transitory computer readable medium for storing program instructions, wherein the computer readable medium includes program instructions causing a computer, by being executed by a processor of the computer to:
   obtain first nuclear-medicine-brain-imaging-data resulting from a first radioisotope-drug-injection and second nuclear-medicine-brain-imaging-data resulting from a second radioisotope-drug-injection;
   obtain, respectively from corresponding storages, a standard input function S(t) which is a function representing temporal changes in inflow of a radioisotope medicine into a standard brain, and $V_d$ which is a cerebral-blood-distribution-coefficient;
   obtain values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively;
   obtain values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;
   create a time activity curve representing a temporal change in counts in a first certain cerebral region, based on the first nuclear-medicine-brain-imaging-data;
   seek $k_{1W}C_f$ and $k_{2W}$ by fitting the time activity curve into the following formula (5'):

$$B_W(t) = k_{1W}C_f \int_{t_0}^{t} S(\tau) \cdot e^{-k_{2W}(t-\tau)} d\tau \tag{5'}$$

wherein $B_W(t)$ is a radiation count obtained from the first nuclear-medicine-brain-imaging-data and is a radiation count in the first certain cerebral region of a first cerebral region at a time of t, $t_0$ represents the time when the first radioisotope-drug-injection took place, $C_f$ is a scaling factor, $k_{1W}$ represents the cerebral blood flow generated in the first certain cerebral region corresponding to the first radioisotope-drug-injection, and $k_{2W}$ represents the blood-outflow-rate-constant in the first certain cerebral region corresponding to the first radioisotope-drug-injection;
   seek $C_f V_d$ based on the following formula (6') from the sought $k_{1W}C_f$ and $k_{2W}$;

$$K_{1W}C_f/k_{2W} = C_f V_d \tag{6'}$$

obtain a correlation formula expressing the relation between a scaling factor $mC_f$ and $C_f V_d$ from a prescribed storage, and seek $mC_f$ by applying the sought $C_f V_d$ to the correlation formula;
   seek $k_1$ utilizing the following formulas (3) or (4) using the sought $mC_f$, where $k_1$ represents the cerebral blood flow generated in a second cerebral region corresponding to the first radioisotope-drug-injection;

$$B(t) = k_1 mC_f \int_{t_0}^{t} S(\tau) \cdot e^{-\frac{k_1}{V_d}(t-\tau)} d\tau \tag{3}$$

$$\int_{t_1}^{t_2} B(t)dt = \int_{t_1}^{t_2} k_1 mC_f \int_{t_0}^{t} S(\tau) \cdot e^{-\frac{k_1}{V_d}(t-\tau)} d\tau dt \tag{4}$$

wherein B(t) is a radiation count obtained from the first nuclear-medicine-brain-imaging-data and is a radiation count of the second cerebral region at a time of t, and $k_2$ is the blood-outflow-rate-constant in the second cerebral region corresponding to the first radioisotope-drug-injection, where $k_2 = k_1/V_d$; and
   seek, utilizing the following formula (1) or (2) using the sought $k_1$, where $k_{1d}$ represents cerebral blood flow generated in the second cerebral region corresponding to the second radioisotope-drug-injection;

$$B_d(t) = k_1 e^{-k_2 t_3} mC_f \int_{t_0}^{t_3} S(\tau) e^{k_2 \tau} d\tau (e^{-k_{2d}(t-t_3)}) + \quad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B_d(t) dt = \quad (2)$$

$$\frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) +$$

$$\int_{t_5}^{t_6} k_{1d} mC_f \int_{t_3}^{t} (S(\tau) + S(\tau - t_3)) \cdot e^{-k_{2d} \cdot (t-\tau)} d\tau dt (t \geq t_3)$$

wherein $B_d(t)$ is a radiation count obtained from the second nuclear-medicine-brain-imaging-data and is a radiation count of the second cerebral region at a time of t, and $k_{2d}$ is the blood-outflow-rate-constant from the second brain tissues corresponding to the second radioisotope-drug-injection, where $k_{2d} = k_{1d}/V_d$.

10. A method for determining cerebral blood flow, including:
    obtaining second nuclear-medicine-brain-imaging-data resulting from a second radioisotope-drug-injection;
    obtaining values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;
    obtaining, respectively from a corresponding storage, a standard input function S(t) which is a function representing temporal changes in inflow of a radioisotope medicine into a standard brain, $mC_f$ which is a scaling factor, $V_d$ which is a cerebral-blood-distribution-coefficient, and $k_1$ which represents the cerebral blood flow generated in a certain cerebral region corresponding to a first radioisotope-drug-injection performed prior to the second radioisotope-drug-injection; and
    seeking, utilizing the following formulas (1) or (2), $k_{1d}$ which represents the cerebral blood flow generated in a certain cerebral region corresponding to the second radioisotope-drug-injection, $$B_d(t) = k_1 e^{-k_2 t_3} mC_f \int_{t_0}^{t_3} S(\tau) e^{k_2 \tau} d\tau (e^{-k_{2d}(t-t_3)}) + \quad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

$$\int_{t_5}^{t_6} B_d(t) dt = \quad (2)$$

$$\frac{k_1}{k_{2d}} e^{-k_2 t_3} mC_f \int_{t_0}^{t_3} S(\tau) e^{k_2 \tau} d\tau \cdot (e^{-k_{2d}(t_5-t_3)} - e^{-k_{2d}(t_6-t_3)}) +$$

$$\int_{t_5}^{t_6} k_{1d} mC_f \int_{t_3}^{t} (S(\tau) + S(\tau - t_3)) \cdot e^{-k_{2d} \cdot (t-\tau)} d\tau dt (t \geq t_3)$$

wherein $B_d(t)$ in formulas (1) or (2) is a radiation count obtained from the second nuclear-medicine-brain-imaging-data and is a radiation count of the certain cerebral region at the time of t, $t_0$ is the time when the first radioisotope-drug- injection took place, $k_2$ is the blood-outflow-rate-constant of brain tissues in the certain cerebral region corresponding to the first radioisotope-drug-injection, where $k_2 = k_1/V_d$, and $k_{2d}$ is the blood-outflow-rate-constant of brain tissues in the certain cerebral region corresponding to the second radioisotope-drug-injection, where $k_{2d} = k_{1d}/V_d$.

11. A method for determining cerebral blood flow, including:
    obtaining first nuclear-medicine-brain-imaging-data resulting from the first radioisotope-drug-injection and second nuclear-medicine-brain-imaging-data resulting from a second radioisotope-drug-injection;
    obtaining, respectively from a corresponding storage, a standard input function S(t) which is a function representing temporal changes in inflow of a radioisotope medicine into a standard brain, $mC_f$ which is a scaling factor, and $V_d$ which is a cerebral-blood-distribution-coefficient;
    obtaining values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively;
    obtaining values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is a time when acquisition of the second nuclear-medicine-brain-imaging-data finished, wherein obtaining is conducted by searching within the second nuclear-medicine-brain-imaging-data or by reading out the values from corresponding storages respectively;
    seeking $k_1$ which represents the cerebral blood flow generated in a certain cerebral region corresponding to the first radioisotope-drug-injection based on the following formulas (3) or (4):

$$B(t) = k_1 mC_f \int_{t_0}^{t} S(\tau) \cdot e^{-\frac{k_1}{V_d} \cdot (t-\tau)} d\tau \quad (3)$$

$$\int_{t_1}^{t_2} B(t) dt = \int_{t_1}^{t_2} k_1 mC_f \int_{t_0}^{t} S(\tau) \cdot e^{-\frac{k_1}{V_d} \cdot (t-\tau)} d\tau dt \quad (4)$$

wherein B(t) is a radiation count obtained from the first nuclear-medicine-brain-imaging-data and is a radiation count of the certain cerebral region at a time of t; and
    seeking $k_{1d}$ which represents the cerebral blood flow generated in the certain cerebral region corresponding to the second radioisotope-drug-injection using the sought $k_1$ and based on the following formulas (1) or (2):

$$B_d(t) = k_1 e^{-k_2 t_3} mC_f \int_{t_0}^{t_3} S(\tau) e^{k_2 \tau} d\tau (e^{-k_{2d}(t-t_3)}) + \quad (1)$$

$$k_{1d} mC_f \int_{t_3}^{t} (S(\tau) + S(\tau - t_3)) \cdot e^{-k_{2d} \cdot (t-\tau)} d\tau (t \geq t_3)$$

-continued $$\int_{t_5}^{t_6} B_d(t)dt = \qquad (2)$$
$$\frac{k_1}{k_{2d}}e^{-k_2 t_3}mC_f\int_{t_0}^{t_3}S(\tau)e^{k_2\tau}d\tau\cdot(e^{-k_{2d}(t_5-t_3)}-e^{-k_{2d}(t_6-t_3)})+$$
$$\int_{t_5}^{t_6}k_{1d}mC_f\int_{t_3}^{t}(S(\tau)+S(\tau-t_3))\cdot e^{-k_{2d}\cdot(t-\tau)}d\tau dt (t\geq t_3)$$

wherein $B_d(t)$ is a radiation count obtained from the second nuclear-medicine-brain-imaging-data and is a radiation count of the second cerebral region at a time of t, $k_2$ is the blood-outflow-rate-constant of brain tissues in the second cerebral region corresponding to the first radioisotope-drug-injection, where $k_2=k_1/V_d$, and $k_{2d}$ is the blood-outflow-rate-constant of brain tissues in the second cerebral region corresponding to the second radioisotope-drug-injection, where $k_{2d}=k_{1d}/V_d$.

12. A method for determining cerebral blood flow, including:
    obtaining first nuclear-medicine-brain-imaging-data resulting from a first radioisotope-drug-injection and second nuclear-medicine-brain-imaging-data resulting from a second radioisotope-drug-injection;
    obtaining, respectively from a corresponding storage, a standard input function S(t) which is a function representing temporal changes in inflow of a radioisotope medicine into a standard brain, and $V_d$ which is a cerebral-blood-distribution-coefficient;
    obtaining values required for a formula that is used in the following formulas (3) or (4) among $t_1$ which is the time when acquisition of the first nuclear-medicine-brain-imaging-data based on the first radioisotope-drug-injection started and $t_2$ which is the time when acquisition of the first nuclear-medicine-brain-imaging-data finished, wherein obtaining is conducted by searching within the first nuclear-medicine-brain-imaging-data or by reading out the values from corresponding storages respectively;
    obtaining values required for a formula that is used in the following formulas (1) or (2) among $t_3$ which is the time when the second radioisotope-drug-injection took place, $t_5$ which is the time when acquisition of the second nuclear-medicine-brain-imaging-data started, and $t_6$ which is the time when acquisition of the second nuclear-medicine-brain-imaging-data finished, wherein obtaining is conducted by searching within the second nuclear-medicine-brain-imaging-data or by reading out the values from corresponding storages respectively;
    creating a time activity curve that represents a temporal change in counts, based on the first nuclear-medicine-brain-imaging-data;
    seeking $k_{1W}C_f$ and $k_{2W}$ by fitting the time activity curve into the following formula (5'):

$$B_W(t)=k_{1W}C_f\int_{t_0}^{t}S(\tau)\cdot e^{-k_{2W}\cdot(t-\tau)}d\tau \qquad (5')$$

wherein $B_W(t)$ is a radiation count obtained from the first nuclear-medicine-brain-imaging-data and is a radiation count of a first cerebral region at the time of t, $t_o$ represents the time when the first radioisotope-drug-injection took place, $C_f$ is a scaling factor, $k_{1W}$ represents the cerebral blood flow generated in the first certain cerebral region corresponding to the first radioisotope-drug-injection, and $k_{2W}$ represents the blood-outflow-rate-constant in the first certain cerebral region corresponding to the first radioisotope-drug-injection;
    seeking $C_fV_d$ based on the following formula (6') from the sought $k_{1W}C_f$ and $k_{2W}$;

$$k_{1W}C_f/k_{2W}=C_fV_d \qquad (6')$$

obtaining a correlation formula expressing the relation between a scaling factor $mC_f$ and $C_fV_d$ from a prescribed storage, and seeking $mC_f$ by applying the sought $C_fV_d$ to the correlation formula;
    seeking $k_1$ which represents cerebral blood flow generated in a second cerebral region corresponding to the first radioisotope-drug-injection using the sought $mC_f$ based on the following formulas (3) or (4):

$$B(t)=k_1mC_f\int_{t_0}^{t}S(\tau)\cdot e^{-\frac{k_1}{V_d}\cdot(t-\tau)}d\tau \qquad (3)$$

$$\int_{t_1}^{t_2}B(t)dt=\int_{t_1}^{t_2}k_1mC_f\int_{t_0}^{t}S(\tau)\cdot e^{-\frac{k_1}{V_d}\cdot(t-\tau)}d\tau dt \qquad (4)$$

wherein B(t) is a radiation count obtained from the first nuclear-medicine-brain-imaging-data and is a radiation count of the second cerebral region at a time of t; and
    seeking $k_{1d}$ which represents the cerebral blood flow generated in the second cerebral region corresponding to the second radioisotope-drug-injection using the sought $k_1$ based on the following formulas (1) or (2):

$$B_d(t)=k_1e^{-k_2 t_3}mC_f\int_{t_0}^{t_3}S(\tau)e^{k_2\tau}d\tau(e^{-k_{2d}(t-t_3)})+ \qquad (1)$$
$$k_{1d}mC_f\int_{t_3}^{t}(S(\tau)+S(\tau-t_3))\cdot e^{-k_{2d}\cdot(t-\tau)}d\tau (t\geq t_3)$$

$$\int_{t_5}^{t_6}B_d(t)dt= \qquad (2)$$
$$\frac{k_1}{k_{2d}}e^{-k_2 t_3}mC_f\int_{t_0}^{t_3}S(\tau)e^{k_2\tau}d\tau\cdot(e^{-k_{2d}(t_5-t_3)}-e^{-k_{2d}(t_6-t_3)})+$$
$$\int_{t_5}^{t_6}k_{1d}mC_f\int_{t_3}^{t}(S(\tau)+S(\tau-t_3))\cdot e^{-k_{2d}\cdot(t-\tau)}d\tau dt (t\geq t_3)$$

wherein $B_d(t)$ is a radiation count obtained from the second nuclear-medicine-brain-imaging-data and is a radiation count of the second cerebral region at a time of t, $k_2$ is the blood-outflow-rate-constant of brain tissues in the second cerebral region corresponding to the first radioisotope-drug-injection, where $k_2=k_1/V_d$, and $k_{2d}$ is the blood-outflow-rate-constant of brain tissues in the second cerebral region corresponding to the second radioisotope-drug-injection, where $k_{2d}=k_{1d}/V_d$.

* * * * *